(12) United States Patent
Tsunemori

(10) Patent No.: US 6,583,339 B1
(45) Date of Patent: Jun. 24, 2003

(54) MANILAGRASS WITH GREEN LEAVES IN WINTER AND ERAGROSTOIDEAE PLANT PRODUCED THEREFROM

(75) Inventor: Itsuki Tsunemori, Hofu (JP)

(73) Assignee: Kaisui Chemical Industry Co., Ltd., Yamaguchi (JP)

( * ) Notice: Subject to any disclaimer, the term of this patent is extended or adjusted under 35 U.S.C. 154(b) by 0 days.

(21) Appl. No.: 09/622,948

(22) PCT Filed: Dec. 28, 1999

(86) PCT No.: PCT/JP99/07426

§ 371 (c)(1),
(2), (4) Date: Aug. 23, 2000

(87) PCT Pub. No.: WO00/38499

PCT Pub. Date: Jul. 6, 2000

(30) Foreign Application Priority Data

Dec. 28, 1998 (JP) .............................. 10-376965

(51) Int. Cl.⁷ .............................. A01H 5/00; A01H 1/06
(52) U.S. Cl. ........................ 800/298; 800/276
(58) Field of Search .............................. 800/276, 266, 800/267, 270, 298

(56) References Cited

U.S. PATENT DOCUMENTS

| | | | |
|---|---|---|---|
| PP5,845 P | 12/1986 | Youngner | |
| PP6,529 P | 1/1989 | Pursley | |
| PP9,089 P | 3/1995 | Yamagishi et al. | |
| PP9,127 P | * 5/1995 | Gibeault et al. | Plt./90 |
| PP10,187 P | 1/1998 | Yaneshita et al. | |

OTHER PUBLICATIONS

"Study of Turf Formation Ratio and Winter Green Retention of New Zoysia Grass Varieties 'De Anza' and Victoria" Kazuhiro Ueda and Hisakazu Kihara, Turf Control Department, Nichino Ryokka Co., Ltd., Dated: Aug. 23, 1995.

\* cited by examiner

*Primary Examiner*—Deborah Crouch
*Assistant Examiner*—Joseph Woitach
(74) *Attorney, Agent, or Firm*—Paul & Paul

(57) ABSTRACT

A series of independent technical systems including a combination of mutation methods such as cellular mutation, ultraviolet irradiation, X-ray irradiation or the like, formation and use of shoot primordium and selection of mutated cells are employed to produce genetic mutation in Manilagrass and obtain Manilagrass that retains its green leaves in winter while producing substantially no anthocyanins under normal cultivating conditions, Manilagrass that has a high stolon density, and dwarfed Manilagrass; the newly invented completely novel genotypes are used to obtain new Eragrostoideae plants.

1 Claim, 22 Drawing Sheets

Absorbance 0.002

971125

980122

980226

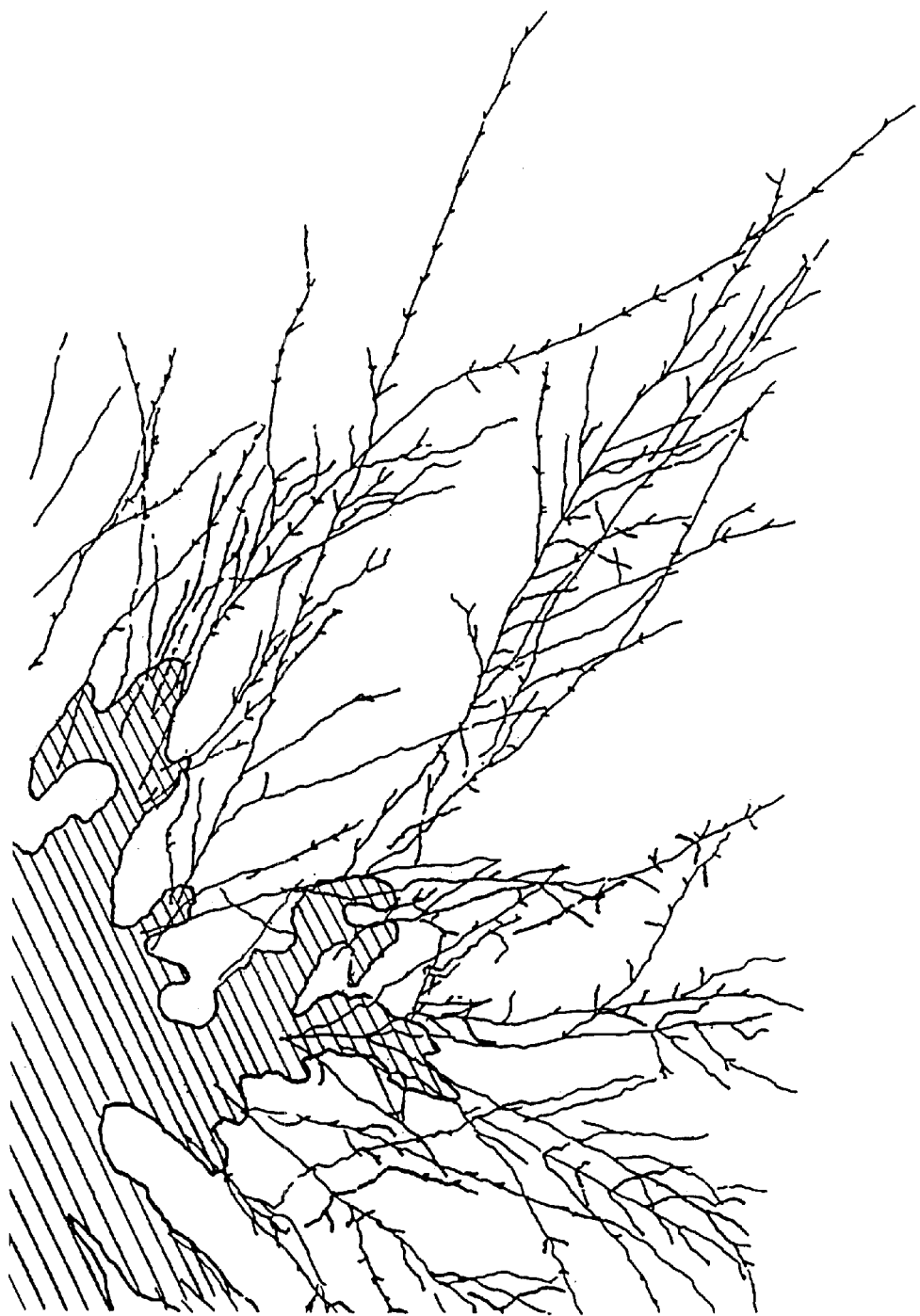

MANILAGRASS WITH GREEN LEAVES IN WINTER AND ERAGROSTOIDEAE PLANT PRODUCED THEREFROM

TECHNICAL FIELD

The present invention relates to plants belonging to a novel Manilagrass variety newly produced by adding a genetic variation to a single line (strain) of *Zoysia matrella* (common name: Manilagrass) without conventional crossbreeding, cell fusion, gene introduction or the like, which variety retains the characteristics of conventional Manilagrass while also exhibiting a completely new character. Specifically, it relates to a novel Manilagrass that retains its green leaves under the same seasonal conditions in which conventional Manilagrass loses its green leaves. The present invention further relates to Manilagrass that retains its green leaves in winter while producing substantially no anthocyanins under normal cultivating conditions, Manilagrass that has a high stolon density, dwarfed Manilagrass, and newly invented Eragrostoideae plant developed using genotypes absent in conventional Manilagrass lines but present in Manilagrass of the invention.

BACKGROUND ART

"Manilagrass" according to the present invention refers to *Zoysia matrella* that exhibits creeping properties by vegetative growth, having a blade width of 1.0–3.5 mm, and it does not include interspecies hybrid lines obtained by artificial crossbreeding with other species such as *Zoysia japonica*, *Zoysia tenuifolia* and *Cynodon dactylon* (see Fukuoka, H., "Turfgrass and Its varieties", ed. by Asano, Y. and Aoki, K., Jun. 15, 1998, Softscience Publications, pp.122–123).

*Zoysia matrella* (common name: Manilagrass) is widely used as a ground cover for a broad range of purposes, because of its many features including aesthetic appearance, ground spread, management ease, wear resistance, water stress resistance, growing power and creeping properties.

However, Manilagrass has certain disadvantages including withered leaf during winter, strong preferential growth of main apical buds, impaired appearance due to anthocyanins, and the need for more frequent trimming in summer due to intensified growth; for these reasons, it not only fails to satisfy market needs but is also limited in its uses.

Specifically, for uses that place importance on aesthetic appearance, for example, sports turfs, open areas such as parks, factory lawns and facility exteriors, rooftop heat-insulating greenery, gardens and the like, withered leaf during winter notably lowers the value of Manilagrass, and the concept of "evergreen Manilagrass" has been a requirement for numerous purposes and would meet a very strong market demand.

In order to compensate for withered leaf in winter of Manilagrass and Bermudagrass (*Cynodon dactylon*), many sports turfs are managed with the overseed method (a method in which Western grass, which is a cool season turfgrass, is sown over Manilagrass areas or Bermudagrass areas at the beginning of autumn in order to maintain the green appearance in winter, and then the western grass is killed off in spring to allow resprouting of the Manilagrass or Bermudagrass), or the withered leaf coloring method (a method in which the withered leaves of Manilagrass are colored with a green pigment or dye). These methods, however, require expensive investment each year leading to notable cost increase and, although they are often employed at golf courses and other sports turfs they are difficult to carry out in practice in most other fields, while the overseeding method also results in yearly weakening of the Manilagrass itself.

Withered leaf in winter of Manilagrass is also a fatal drawback for rooftop heat-insulating greenery, used for its effectiveness toward energy reduction and carbon dioxide gas fixation.

Withered leaf in winter of Manilagrass and Bermudagrass tends to result in bare ground due to the wearing that occurs with trampling, etc., and a further drawback, in the case of Manilagrass, is its susceptibility to winter weeds and spring sprouting weeds, which tend to promote turfgrass decay.

In addition to physical methods such as the overseed method and the withered leaf coloring method, the following measures have also been adopted to shorten the withered leaf in winter period of Eragrostoideae turfgrass.

(a) Dispersion of iron chemicals: Iron absorption promotes chlorophyll synthesis to increase the greenness of the plants.

(b) Dispersion of nitrogen fertilizers: This method is effective for maintaining greenness during the initial winter period but it also delays sprouting in spring, and because the withered leaf in winter period is not significantly shortened it is not a preferred method.

(c) Dispersion of 5-aminolevulinic acid (ALA): This has been reported to have a chlorophyll-increasing effect ("5-Aminolevulinic Acid: Applications for Microbe Production and Lawngrass", Hotta, Y., Tanaka, T., Watanabe, K., Takeuchi, Y., Konnai, M., "Lawngrass Research" meeting journal, No.27, 1998, pp.138–139).

(d) Breeding methods: It has been attempted to crossbreed *Zoysia matrella* and *Zoysia japonica*, for example, to solve the problem of withered leaf in winter. Further collection and selection of regional lines throughout the world have also been attempted in order to obtain varieties with favorable genotypes, for example, by selection of lines with minimal withered leaf in winter. (For example, Fukuoka, H., "Turfgrass and Its Varieties", ed. by Asano, Y. and Aoki, K., Softscience Publications, Chap. 3, 3–2, pp.126–130). However, crossbreeding *Zoysia matrella* with other varieties tends to lessen the features of Manilagrass, with the resulting varieties having wider blade widths and inferior aesthetic appearance compared to *Zoysia matrella*, while the problem of withered leaf in winter is not satisfactorily solved. On the other hand, methods involving the latter collection of lines mentioned above have to date failed to provide Manilagrass with sufficient greenness in winter.

DISCLOSURE OF THE INVENTION

The present invention relates to Manilagrass characterized by retaining its green leaves under a condition where the mean temperature of a period of ten days is 6° C. or below and the lowest temperature in this period is −1° C. or below, but not less than −15° C., and by containing substantially no anthocyanins throughout the year.

The invention further relates to the aforementioned Manilagrass, characterized in that the length of the internode of a main stolon except the immature internodes of the front part of the main stolon, which extends when attached to the soil surface under obstacle-free growth conditions, is about 0.9—about 0.6, where 1.0 is defined as the length for conventional Tottori *Z. matrella* (Tottori Sod Producers Association: the representative Manilagrass single line produced and marketed at 558-1 Oaza-Tokuman, Tohaku-cho, Tohaku-gun; Tottori, Japan).

The invention still further relates to each aforementioned Manilagrass, characterized in that the ratio of the main stolon length to the total lateral stolon length, measuring the total length of lateral stolons developing from the main stolon based on a main stolon length corresponding to at least 20 nodes from the tip of the main stolon of the turigrass of the invention, in stolons extending under obstacle-free growth conditions when attached to the soil surface, is at least 1.2 times compared to conventional Tottori Z. matrella.

The invention still further relates to Eragrostoideae plant bred from any of the aforementioned Manilagrass as the parental strain by crossbreeding, mutation, cell fusion or gene introduction, that inherits any of the aforementioned characteristics.

The novel Manilagrass of the invention has notably higher lateral stolon extendibility compared to the parental strain (Tottori Z. matrella) or Japanese lawngrass (Zoysia japonica), and thus has a higher stolon density, forms a stratified mesh mat earlier and has much higher value for practical use.

Formation of a stratified mesh mat offers the following merits:

(1) Because growth (vegetative propagation) of Manilagrass by seed is difficult in practice, productivity can be improved as the method adopted is to strip a 1–2 cm upper layer, as harvest, each year from the production farm, and repopulate the grass from the remaining mat for harvest the following year;

(2) It is resistant to wearing;

(3) It can be rapidly reproduced even when the upper layer portion has been cut away (for example, as golf course divots);

(4) It increases cushioning properties for sports turf;

(5) It improves drying resistance properties (water retention, water absorption, water storage in plant body);

(6) It greatly improves the spread essential for slopes, riverbeds, etc., and thus helps protect surface soil layers;

(7) It is dense and gives attractive lawn tops;

(8) It can reduce weeds by the formation of dense turfs.

In addition, conventional Manilagrass produces anthocyanins and colors in the stems throughout the year and undergoes coloration, while anthocyanins are produced resulting in coloration even in the few living leaves remaining under daily mean temperatures of lower than about 10° C., such that it presents a purplish red, dark green-purple or blackish-purple color, thereby losing much of its attractive green appearance. According to the present invention, however, the aforementioned problem is solved by providing the first variety of Manilagrass to contain substantially no anthocyanins.

In order to ensure high quality lawn tops for golf course fairways and the like, they must be mowed about 2–3 times per week during the high temperature growth season, and in some cases growth retardants are dispersed on purpose to reduce the mowing frequency. This leads to a notable increase in maintenance costs. The Manilagrass of the invention also provides an improvement in this respect.

It is an object of the present invention to provide a new variety of Manilagrass that retains its green leaves in winter while containing substantially no anthocyanins throughout the year, as well as dwarfed Manilagrass, Manilagrass that has a high stolon density, and Eragrostoideae plant incorporating genotypes of the Manilagrass newly developed according to the invention.

For the purpose of the present invention, the term "winter" will refer to the low temperature period in which conventional Manilagrass, which is the starting material for the invention, experiences loss of green leaves and undergoes coloration to brown or dried grass color under common practical outdoor cultivating conditions, and for example, Tottori Z. matrella at the research field of Kaisui Chemical Industry Co., Ltd. experiences withered leaf in early January, becoming dried grass colored across the entire covered region.

The mean measured temperature of a period of ten days for early January, 1999 was 6.6° C., with a low temperature of −0.8° C. Table 1 shows the weather conditions from mid December, 1998 to early March, 1999 at the abovementioned research field.

TABLE 1

Weather conditions from Dec. 11, 1998 to Mar. 10, 1999 at research field of Kaisui Chemical Industry Co., Ltd.

| Yr.Mon.Day | | | Mean temperature (° C.) | Highest temperature (° C.) | Lowest temperature (° C.) | Total sunlight (MJ/m$^2$) |
|---|---|---|---|---|---|---|
| 1998 | 12 | 11 | 5.7 | 10.4 | 1.7 | 5.2 |
| | | 12 | 5.6 | 11.2 | 1.4 | 8.9 |
| | | 13 | 7.3 | 14.0 | 1.4 | 7.6 |
| | | 14 | 9.8 | 15.1 | 2.8 | 5.4 |
| | | 15 | 10.3 | 13.3 | 6.4 | 4.5 |
| | | 16 | 8.4 | 14.2 | 4.2 | 5.3 |
| | | 17 | 8.6 | 16.7 | 3.4 | 8.8 |
| | | 18 | 8.3 | 15.6 | 3.3 | 7.0 |
| | | 19 | 10.1 | 16.8 | 3.8 | 6.7 |
| | | 20 | 10.4 | 14.4 | 4.6 | 9.0 |
| Mid ten days of the month | | | 8.5 | 16.8 | 1.4 | 68.4 |
| | | 21 | 6.9 | 13.7 | 1.5 | 9.0 |
| | | 22 | 8.4 | 16.5 | 2.5 | 8.7 |
| | | 23 | 9.7 | 15.2 | 4.7 | 6.3 |
| | | 24 | 8.4 | 11.5 | 5.0 | 2.5 |
| | | 25 | 6.8 | 11.4 | 3.1 | 9.0 |
| | | 26 | 7.9 | 13.9 | 2.8 | 8.4 |
| | | 27 | 8.1 | 13.8 | 4.4 | 4.4 |
| | | 28 | 8.0 | 13.8 | 3.4 | 6.8 |
| | | 29 | 8.0 | 14.5 | 3.7 | 5.6 |
| | | 30 | 6.9 | 11.0 | 4.2 | 9.0 |
| Late ten days of the month | | | 7.9 | 16.5 | 1.5 | 69.7 |
| | 12 | 31 | 5.7 | 9.0 | 1.7 | 7.0 |
| 1999 | 1 | 1 | 4.4 | 10.1 | 0.2 | 8.2 |
| | | 2 | 5.3 | 9.5 | 0.0 | 1.9 |
| | | 3 | 6.0 | 12.4 | 0.9 | 5.3 |
| | | 4 | 6.3 | 12.9 | 1.2 | 7.3 |
| | | 5 | 5.8 | 12.9 | 0.9 | 8.9 |
| | | 6 | 7.1 | 13.3 | 2.1 | 2.3 |
| | | 7 | 6.5 | 10.2 | 0.3 | 4.2 |
| | | 8 | 9.0 | 2.9 | −0.6 | 4.5 |
| | | 9 | 10.0 | 2.8 | −0.8 | 6.4 |
| Early ten days of the month | | | 6.6 | 13.3 | −0.8 | 56.0 |
| | | 10 | 3.1 | 6.2 | 0.4 | 7.0 |
| | | 11 | 4.3 | 7.2 | 1.9 | 6.4 |
| | | 12 | 4.0 | 7.5 | −0.6 | 5.5 |
| | | 13 | 3.8 | 8.8 | −2.3 | 8.1 |
| | | 14 | 5.1 | 10.4 | −1.2 | 6.7 |
| | | 15 | 3.5 | 6.5 | −1.3 | 2.2 |
| | | 16 | 3.2 | 7.8 | −1.7 | 3.0 |
| | | 17 | 4.4 | 9.3 | 0.9 | 7.8 |

TABLE 1-continued

Weather conditions from Dec. 11, 1998 to
Mar. 10, 1999 at research field of Kaisui Chemical
Industry Co., Ltd.

| Yr.Mon.Day | | | Mean temperature (° C.) | Highest temperature (° C.) | Lowest temperature (° C.) | Total sunlight (MJ/m$^2$) |
|---|---|---|---|---|---|---|
| | | 18 | 5.5 | 12.4 | −0.4 | 6.2 |
| | | 19 | 8.8 | 12.6 | 3.9 | 1.2 |
| | Mid ten days of the month | | 4.6 | 12.6 | −2.3 | 54.1 |
| | | 20 | 6.4 | 12.7 | 2.1 | 7.2 |
| | | 21 | 3.6 | 8.1 | −1.2 | 6.7 |
| | | 22 | 3.7 | 10.5 | −1.9 | 7.6 |
| | | 23 | 7.2 | 13.3 | 1.2 | 4.1 |
| | | 24 | 8.7 | 13.2 | 4.6 | 4.2 |
| | | 25 | 8.1 | 12.6 | 3.1 | 2.7 |
| | | 26 | 7.5 | 11.9 | 1.0 | 8.7 |
| | | 27 | 5.8 | 10.7 | 0.0 | 2.2 |
| | | 28 | 6.3 | 11.4 | 0.4 | 7.9 |
| | | 29 | 3.2 | 9.0 | −0.9 | 4.9 |
| | Late ten days of the month | | 6.1 | 13.3 | −1.9 | 56.2 |
| 1999 | 1 | 30 | 3.3 | 9.0 | −2.0 | 9.1 |
| | | 31 | 5.3 | 10.4 | −0.6 | 8.1 |
| | 2 | 1 | 7.6 | 12.9 | 3.7 | 1.3 |
| | | 2 | 5.7 | 9.2 | 1.3 | 5.1 |
| | | 3 | −0.3 | 1.7 | −2.5 | 7.2 |
| | | 4 | 0.1 | 4.6 | −5.2 | 2.9 |
| | | 5 | 3.4 | 6.9 | 0.5 | 6.7 |
| | | 6 | 4.0 | 9.5 | −0.9 | 8.5 |
| | | 7 | 5.2 | 13.0 | −0.9 | 9.5 |
| | | 8 | 6.0 | 14.0 | 0.5 | 7.8 |
| | Early ten days of the month | | 4.0 | 14.0 | −5.2 | 66.2 |
| | | 9 | 6.4 | 13.8 | 0.3 | 8.5 |
| | | 10 | 7.9 | 12.8 | 1.8 | 5.6 |
| | | 11 | 6.8 | 8.3 | 3.6 | 2.5 |
| | | 12 | 4.4 | 6.3 | 1.2 | 3.6 |
| | | 13 | 1.9 | 5.7 | −1.9 | 9.2 |
| | | 14 | 2.6 | 9.8 | −2.6 | 8.3 |
| | | 15 | 4.2 | 10.4 | −0.4 | 7.2 |
| | | 16 | 5.7 | 12.5 | 0.0 | 9.3 |
| | | 17 | 7.9 | 15.9 | 0.8 | 8.9 |
| | | 18 | 8.4 | 10.6 | 5.3 | 0.0 |
| | Mid ten days of the month | | 5.6 | 15.9 | −2.6 | 63.1 |
| | | 19 | 4.6 | 7.2 | 0.4 | 5.3 |
| | | 20 | 2.3 | 4.3 | −0.6 | 3.0 |
| | | 21 | 2.7 | 5.4 | −1.9 | 7.1 |
| | | 22 | 3.8 | 8.7 | −1.8 | 1.7 |
| | | 23 | 6.5 | 11.2 | 1.5 | 5.4 |
| | | 24 | 7.8 | 9.6 | 5.3 | 0.0 |
| | | 25 | 9.6 | 13.3 | 5.2 | 7.3 |
| | | 26 | 9.0 | 12.1 | 3.5 | 0.0 |
| | | 27 | 8.4 | 11.4 | 2.2 | 7.3 |
| | | 28 | 4.8 | 10.4 | −0.2 | 9.2 |
| | Late ten days of the month | | 6.0 | 13.3 | −1.9 | 46.3 |
| | 3 | 1 | 7.0 | 12.0 | 1.6 | 5.2 |
| | | 2 | 9.3 | 16.4 | 2.6 | 5.4 |
| | | 3 | 9.8 | 17.4 | 4.0 | 10.2 |
| | | 4 | 8.9 | 14.6 | 3.3 | 1.1 |
| | | 5 | 14.5 | 19.6 | 10.7 | 1.5 |
| | | 6 | 11.0 | 16.4 | 5.8 | 10.0 |
| | | 7 | 9.3 | 11.6 | 7.6 | 0.0 |
| | | 8 | 9.4 | 13.5 | 7.1 | 6.7 |
| | | 9 | 7.1 | 8.7 | 3.8 | 0.0 |
| | | 10 | 7.2 | 10.9 | 2.9 | 3.7 |
| | Early ten days of the month | | 9.4 | 19.6 | 1.6 | 43.8 |

Considering the different temperature fluctuation patterns in different years, winter was defined as conditions where the mean temperature of a period of ten days is around 6° C. or below and the lowest temperature of this period is −1° C. or below. Since the lower temperature limit could not be evaluated in the field experiment, a hardening test was conducted as in Example 3 and FIG. 12, and the lower temperature limit was found to be −15° C.

"Maintaining green leaves" means maintaining a green to yellow-green color without turning brown or dried grass colored or undergoing change to purplish red, dark green-purple or blackish-purple color even in the few remaining living leaves during winter, as occurs with conventional Manilagrass, and clearly maintaining a condition recognized as "green" across the entire covered region.

According to the invention, "throughout the year" means that the varieties of the invention maintain green to yellow-green stems, leaves and spikes throughout the year in periods and regions in which conventional Manilagrass contains anthocyanins in the stems, leaves or spikes depending on the season and undergoes coloration to purplish red, dark green-purple or blackish-purple, and "containing substantially no anthocyanins" means not only that no purplish red, dark green-purple or blackish-purple coloration is visually found on the ground areas, but also that anthocyanins are absent (undetectable) or present in only trace amounts based on analysis results for the season and plant parts in which conventional Manilagrass undergoes coloration due to anthocyanins, as explained in the examples given below.

According to the invention, the "immature internodes of the front part of the main stolon" are the section in which the internodes, at the front part of the main stolon including the shoot apex, is still undergoing vegetative growth.

A "parental strain" according to the invention means a strain used as the starting material for crossbreeding, mutation, cell fusion or gene introduction.

As mentioned above, turfgrass has been subjected to seeding methods for the purpose of increasing green color in winter, and has been used for attempted crossbreeding to shorten the dormant period. However, the results obtained by such methods have not satisfied the market need.

All conventional Manilagrass, to a widely varying degree depending on the cultivating region and variety line, experiences withered leaf and browning during winter with reduction in chlorophyll in the barely living sections, while anthocyanins also accumulate in large amounts, such that blackish-purple coloration occurs. Thus, in order to improve the greenness in winter it is necessary to increase the living leaves or inhibit decomposition of chlorophyll while inhibiting production of anthocyanins, while it is also necessary to minimize freezing of living leaves by frost and prevent any notable chlorosis (decomposition of chlorophyll); high wear resistance is also preferred for low temperature growth stagnation periods, but no Manilagrass obtained by conventional methods has yet exhibited the properties that are the object of the present invention. According to the invention, the line having gene mutation inducing novel genotypes, characterized by maintaining green leaves during winter, preventing accumulation of anthocyanin, and having properties described in claims 2–3, which are not found in the parental strain and any other conventional Manilagrass by genetically mutating manipulation on the parental strain, was successfully created.

The Manilagrass of the invention thus contains well-defined purposive conversion induced in the parental strain line, by a series of independent technical systems including a combination of mutation methods such as cellular mutation, ultraviolet irradiation, X-ray irradiation or the like, formation and use of a kind of shoot primordia and selection of transmutated cells as a process for creating a transmutated variety with a direction toward the prescribed goal. The invention has created completely new genotypes that retain the features of Manilagrass such as a narrow blade width and resistance to frozen withered leaf due to frost, while also: (1) retaining green leaves at low temperature even though it is Manilagrass, (2) containing substantially no anthocyanins, (3) having a short internode length, and (4) having high lateral stolon growth; this has been achieved without relying on conventional methods such as natural hybridization, artificial crossbreeding, cell fusion, gene introduction or selection of wild varieties. These genotypes are fixed and are not genotypes obtained by transfer or introduction from other varieties but rather are completely new Manilagrass genotypes. The scope of the invention therefore encompasses Eragrostoideae plant with the features of the invention, obtained by adding further mutation using the variety of the invention, by introducing other genes therein, or by using conventional methods such as crossbreeding for introduction of the new genotypes of the variety.

BRIEF DESCRIPTION OF THE DRAWINGS

FIG. 13 is a photograph at a research field in which 5-node stolons are planted, where

Figure 1:
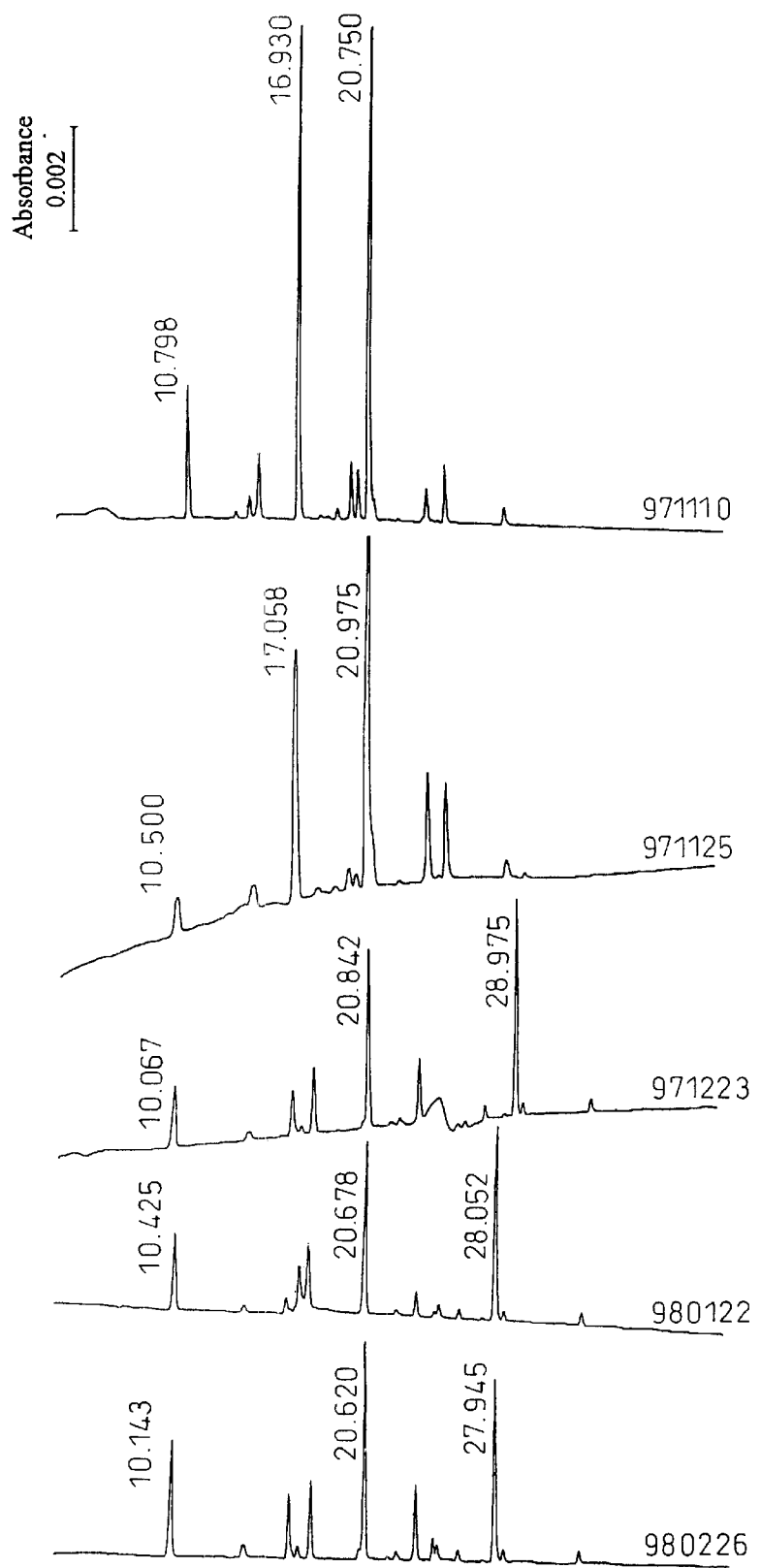
FIG. 1 shows the changes in anthocyanins in the stolons of Tottori Z. matrella according to HPLC, for Nov. 10, 1997, Nov. 25, 1997, Dec. 23, 1997, Jan. 22, 1998 and Feb. 26, 1998 in order from top to bottom.

Shown from top to bottom are the stolons for:
A) TK-XG1
B) Tottori Z. matrella
C) Wintercarpet
D) Winterfield
E) Victoria
F) Miyako
G) Meyer
H) Emerald

DETAILED DESCRIPTION OF THE INVENTION

As explained above, in order to solve the different problems of the prior art, i.e. the problems associated with conventional Manilagrass varieties and lines, the present invention has succeeded in adding intentional mutations to conventional Manilagrass and thereby providing fixed new genotypes. The production method will now be described.
Production Method After using alcohol or a chlorine-based sterilizer to sterilize Manilagrass mature seed embryo tissue, immature seed embryo tissue and apical growth point, axillary bud growth point or shoot apex tissue, the cellular tissue is collected and planted in a Murashige-Skoog medium containing a plant growth regulating substance such as 2,4-dichlorophenoxyacetic acid or indoleacetic acid, and culturing is carried out in aseptic light or dark conditions while the medium is stationary or vibrated, to obtain shoot primordium (see Japanese Unexamined Patent Publication No. 6-106427); the shoot primordium are irradiated with high energy such as ultraviolet rays, soft X-rays or gamma rays or immersed in a mutagenic substance to induce genetic mutation and are then further cultured by replanting in the Murashige-Skoog medium, selection is made based on differences in low temperature sensitivity, and then after further replanting in Murashige-Skoog medium containing no plant growth regulating substance the plant bodies are reproduced and grown to young plants. The young plants are then grown. Acclimatization proceeds very smoothly.

The shoot primordium form domes with a surface structure, and differ from calli that are void of surface structure. The shoot primordium also form aggregates by continued culturing under conditions that produced the shoot primordium, and when these are planted in solid medium containing no plant growth regulating substance, they can reproduce to plant bodies.

Immersion treatment in a mutagenic substance involves addition and dissolution of a mutagenic substance in a liquid medium, buffer solution or the like and immersion of the shoot primordium therein to induce mutation. Mutation-inducing mutagenic substances that may be used include 5-bromo-2'-deoxyuridine, ethylmethane sulfonate (EMS), ethyleneimine (EI), N-methyl-N'-nitro-N-nitrosoguanidine (MNNG), N-nitroso-N'-methylurea (MNH), diethylsulfate, 1,2-epoxybutane, 2,3-epoxypropionic aldehyde, 8-azaguanine, 5-bromouracil, acridine orange, ICR-10, acriflavin and the like.

EXAMPLE 1

Production of Shoot Primordium

Stolon apical buds in the shoot apex tissue of Tottori Z. matrella, a representative Manilagrass line produced and sold by the Tottori Sod Producers Association, were collected and promptly rinsed with a 70% (V/V) ethanol aqueous solution, after which they were sterilized in a 1% (V/V) sodium hypochlorite aqueous solution while slowly shaking for 15 minutes and thoroughly rinsed with sterilized water, and then the shoot apex tissue was planted into solid medium in a vessel by an aseptic procedure in a clean room. The solid medium was a basic medium obtained by adding 30 g of sucrose and 7 g of agar to 1000 ml of Murashige-Skoog medium, and further adding 2 mg of 2,4-dichlorophenoxyacetic acid to adjust the pH to 5.8. Culturing was then carried out at 25° C. in darkness. At about 2 weeks after the start of culturing, calli containing a shoot primordium were obtained as derivatives. The shoot primordium section was cut off and subcultured by the same method to obtain a clump of pure shoot primordium.

Mutation Treatment by Irradiation

A culturing plate was prepared using 20 ml of Murashige-Skoog medium containing 3% sucrose, 0.8% agar and no plant growth regulating substance in a 90-mm diameter plastic Petri dish. The aforementioned clump of shoot primordium cell with a diameter of 2–3 mm was transferred at about 200 per plate and after covering with a quartz disk lid it was sealed with tape. The procedure was carried out aseptically in a clean room. The X-ray irradiation apparatus used was a Model OM-100R irradiating X-ray generator by Ohmic, KK. The ultraviolet ray source used was an HP-30C by Atto, KK. having a wavelength of 254 nm and a beam intensity of 1780 $\mu w/cm^2$. The X-ray irradiation intensity was 60 KVp, 4 mA, the distance to the target was 500 mm, and a 0.5 mm Al filter was used for 25 hours of irradiation. A portion of the apparatus was modified, and the ultraviolet source was placed in the X-ray irradiation cabinet and irradiation was carried out simultaneously with the ultraviolet beam from a distance of 45 cm from the target. Six plates were irradiated at a time, and the procedure was repeated 10 times from October 2 to Oct. 20, 1995.

Culturing to Young Plants

The irradiation-treated plates were allowed to stand in darkness at 28° C. for 2 days. Selection was then performed by low temperature culturing. The shoot primordium were transferred onto Murashige-Skoog plate containing 3% sucrose, 0.8% agar and no plant growth regulating substance that had been prepared in a glass bottle with an inner diameter of 80 mm and a height of 120 mm, and culturing was carried out for 3 months with a cycle of 16 hours at 15° C. under 10,000 lux light and 8 hours at 10° C. in darkness.

This low temperature culturing produced green shoot primordium and purplish red shoot primordium with accumulated anthocyanins. The green shoot primordium were selected out and transferred onto agar medium of the same composition prepared in a wide-rim bottle with an inner diameter of 80 mm and a height of 120 mm and cultured at 28° C. under 4,500–5,000 lux to produce shoots with roots for raising of young plants.

A total of 6,017 green shoot primordium were found among the 12,800 irradiated bodies, and approximately 300 plant were reproduced from these up to March of 1996.

Selection of Target Individuals

Each of the young plants obtained by the procedure described above was transplanted into a #3 pot containing a culturing soil composition of sand earth:vermiculite:peat moss (Lamex Co.) at 2:1:1, and was allowed to grow outdoors. The soil used contained no fertilizer, but as an added fertilizer there was provided each week a liquid fertilizer containing 5 g nitrogen/10 g phosphoric acid/5 g potassium per 100 g (Household gardening fertilizer: Hyponex 5-10-10, Hyponex Japan), diluted 1000-fold, at 50 ml per pot. In addition, a 2% citric acid soluble slow acting fertilizer containing 6 g nitrogen/38 g phosphoric acid/6 g potassium/18 g magnesium per 100 g (Greenmap II,M: Nihon Godo Hiryo, KK.) was added at 1 g per pot on Sep. 12, 1996. Irrigation was carried out daily except for rainy days, for a period of 6 months until attachment to the soil. Acclimatization proceeded very satisfactorily without any special steps. No herbicides, antimicrobial agents or pesticides were used. The outdoor cultivation was at the research field of Kaisui Chemical Industry Co., Ltd. at 535 Hamakata, Hofu City, Yamaguchi Prefecture, Japan, and the winter green leaf retention, growth properties and the period of greening in spring were examined.

The stem color was examined by visually determining the presence or absence of purplish red pigment formation on May 16, Aug. 10 and Dec. 2, 1996. On May 16 the stolons were still undeveloped and the color of the vertical stems was recorded. In the following two examinations the color of the stolons was recorded.

TABLE 2

Changes in stem color of plants reproduced from shoot primordium after irradiation and low temperature selection (1996)

| Stem color | May 16 | August 10 | December 2 |
|---|---|---|---|
| Green | 6 | 1 | 1 |
| Purplish red | 239 | 244 | 244 |
| Withered | 62 | 62 | 62 |
| Total | 307 | 307 | 307 |

Six plants exhibited green vertical stems by the first examination, but in the succeeding examinations only one plant failed to exhibit a purplish red color in both the vertical stems and stolons.

The degree of greenness of the leaves in winter was evaluated visually on Dec. 2, 1996 and evaluated based on a 5-level scale.

TABLE 3

Selection based on greenness retained in winter

| Greenness | Dec. 2, 1996 | Jan. 31, 1997 | Feb. 14, 1997 | Feb. 14, 1999 |
|---|---|---|---|---|
| 5 | 2 | 0 | 0 | 0 |
| 4 | 9 | 1 | 1 | 1 |
| 3 | 234 | 0 | 0 | 0 |

TABLE 3-continued

Selection based on greenness retained in winter

| Greenness | Dec. 2, 1996 | Jan. 31, 1997 | Feb. 14, 1997 | Feb. 14, 1999 |
|---|---|---|---|---|
| 2 | 0 | 14 | 11 | 0 |
| 1 | 0 | 230 | 233 | 234 |
| Withered | 62 | 62 | 62 | 62 |
| Total | 307 | 307 | 307 | 307 |

5 - Totally green leaves
4 - Some totally green live leaf blades exhibiting no purplish red or yellow color, with some withered leaf blades exhibiting loss of greenness
3 - Some 1–2 mm blade tips exhibiting purplish red or yellow color
2 - Greenness remaining only at base of leaf blades
1 - No greenness throughout entire variety A variety was selected that exhibited no purplish red pigmentation of stems or leaves even by February 14 during the above outdoor winter selection, and this variety was designated as Line No. 42-289.

Evaluation of Character

Variety No. 42-289 obtained in the manner described above was transferred to three planters on Oct. 22, 1996, the line name was changed to TK-XG1, and the plants were raised in a greenhouse and allowed to grow and observed until the next Jun. 30, 1997. From September 1997, they were transferred to a research field together with 7 control varieties and the characteristics of each were evaluated by a 2.0 m square section at 1 location in the dense planted section and at 2 locations in the sparse planted section. The soil components of the field were masatsuchi: native weathered soil from granite and sand in a mixture of 7:3, with hard sintered diatomite foamed granules (Isolite: Isolite Industries, KK.) at 100 kg/m$^3$, 2% citric acid soluble slow acting fertilizer at 1.5 kg/m$^3$ and a special fermented fertilizer (Mothersoil: Koto Industries, KK.) at 10 kg/m$^3$. In each dense planted section, 81 young plants each with 5-node stolons were transplanted at a spacing of 15 cm. In each sparse planted section, one young plant each with 5-node stolons was transplanted at the center. The fertilizer was evenly dispersed once a month for the 10 months from February to November, to a yearly dose of 20 g/m$^2$ each for nitrogen, phosphoric acid and potassium.

The characteristics of the dense planted sections examined up to February, 1999 are shown in Table 4. As concerns retention of green leaves during the low temperature period, TK-XG1 retained green leaves during the period from May, 1996 to November, 1999, while the Tottori *Z. matrella* lost its green appearance from mid November as it exhibited anthocyanin colored leaves due to anthocyanin coloration and withering of almost all the leaves by late December, and showing dark green coloration or blackish-purple coloration even in those few living leaves that remained. The Meyer, Emerald or common Japanese lawngrass (*Zoysia japonica*) used for comparison all exhibited purplish coloration due to anthocyanins from mid December, with all of the leaves reaching a withered condition by the end of December. The major object of the present invention, which is the feature of producing no anthocyanins, has been visually observed and was substantiated by the analysis described below. The other features were also confirmed as stable characteristics.

TABLE 4

Comparison of features of TK-XG1 and Tottori *Z. matrella* (parental strain, or TK-XG1 starting material)

| | *Zoysia matrella* (TK-XG1) | *Zoysia matrella* (Tottori *Z. matrella*) |
|---|---|---|
| Anthocyanins | | |
| Stolons | Trace 17–min and 20–min HPLC peaks | Anthocyanins detected throughout the year; purplish red color |
| Leaves | No detectable HPLC peak | Detection of same anthocyanins as stolons from autumn through winter |
| Florets | No anthocyanins | Dark purple color |
| Anthers | No anthocyanins | Purplish red color |
| Stolon extension | (after transplanting 5 nodes previous autumn) | |
| Spring–summer | Shorter internodes and more notable lateral stolon growth than Tottori *Z. matrella* | — |
| Early winter | Extension of stolons from end of Nov. to early Dec. | Extension of stolons from end of Oct. to early Nov. |
| Winter (greenhouse) | New stolons produced | No extension of stolons |
| Stolon density[1] | 125.7 | 82.3 |
| Stolon thickness[2] | 1.1 mm | 1.3 mm |
| Spikes | | |
| Spike production period | Spikes produced in winter, beginning later than Tottori *Z. matrella* | Spikes produced all at once in Dec. |
| Blade length[3] | 2.3 cm | 2.4 cm |
| Blade width[4] | 2.1 mm | 2.3 mm |

[1] Average value at 3 locations for the number of stolons crossing a 1.5 m string stretched parallel to the east-west side of the dense planted section
[2] Average value of 10 stolons for the diameter at a section between nodes 4 and 5 from the tip of the stolons
[3] Average value of 10 leaves for the blade length in early summer.
[4] Average value of 10 leaves for the maximum blade width in early summer.

The Tottori *Z. matrella* had purplish red ears while the TK-XG1 formed yellow-green ears with no purplish red color.

The temperatures at the research field of Kaisui Chemical Industry Co., Ltd. during the examination period are listed in Table 5.

TABLE 5

| Year or Month 1996 | Mean temperature (° C.) | Highest temperature (° C.) | Lowest temperature (° C.) | Month 1997 | Mean temperature (° C.) | Highest temperature (° C.) | Lowest temperature (° C.) | Month 1998 | Mean temperature (° C.) | Highest temperature (° C.) | Lowest temperature (° C.) |
|---|---|---|---|---|---|---|---|---|---|---|---|
| Jan | 4.0 | 13.5 | −4.0 | Jan | 3.7 | 15.5 | −3.5 | Jan | 4.8 | 12.0 | −4.0 |
| Feb | 3.0 | 18.5 | −6.0 | Feb | 5.0 | 15.3 | −3.8 | Feb | 7.3 | 19.0 | −2.0 |
| Mar | 7.2 | 17.5 | −3.5 | Mar | 9.4 | 18.2 | 0.0 | Mar | 8.9 | 22.5 | −1.5 |

TABLE 5-continued

| Year or Month 1996 | Mean temperature (° C.) | Highest temperature (° C.) | Lowest temperature (° C.) | Month 1997 | Mean temperature (° C.) | Highest temperature (° C.) | Lowest temperature (° C.) | Month 1998 | Mean temperature (° C.) | Highest temperature (° C.) | Lowest temperature (° C.) |
|---|---|---|---|---|---|---|---|---|---|---|---|
| Apr | 10.3 | 26.0 | −1.0 | Apr | 13.3 | 22.0 | 0.5 | Apr | 15.9 | 19.2 | 13.1 |
| May | 17.5 | 28.5 | 3.5 | May | 18.5 | 27.0 | 8.0 | May | 19.7 | 23.0 | 16.0 |
| Jun | 21.8 | 29.0 | 14.5 | Jun | 22.1 | 30.0 | 14.5 | Jun | 21.7 | 24.6 | 19.4 |
| Jul | 26.0 | 33.0 | 17.5 | Jul | 25.3 | 32.0 | 18.5 | Jul | 27.5 | 29.7 | 23.9 |
| Aug | 27.3 | 33.0 | 20.0 | Aug | 26.8 | 32.0 | 20.0 | Aug | 27.9 | 31.4 | 24.9 |
| Sep | 22.8 | 30.0 | 14.0 | Sep | 22.9 | 33.0 | 12.5 | Sep | 24.4 | 28.7 | 21.7 |
| Oct | 17.2 | 26.5 | 4.5 | Oct | 16.5 | 25.0 | 4.5 | Oct | 19.5 | 22.9 | 16.3 |
| Nov | 12.4 | 23.0 | 2.0 | Nov | 13.2 | 21.5 | 1.5 | | | | |
| Dec | 6.1 | 15.0 | −1.5 | Dec | 7.6 | 16.5 | 0.0 | | | | |

Confirmation of Anthocyanins by High Performance Liquid Chromatography (HPLC)

The leaf blades and stolons of Tottori Z. *matrella* and TK-XG1 were collected separately, and the node sections of the stolons were cut off to leave only the internodes which were then used as samples for anthocyanin analysis. The weight was precisely measured and sea sand was added, and after grinding, 30 ml of 0.1% methanol hydrochloride was added as an extraction solvent and the mixture was allowed to stand for a day and a night. The extract was filtered with No.2 filter paper and the extraction solvent was added to 50 ml. For measurement by HPLC (High Performance Liquid Chromatography), the filtered substance from a membrane filter (0.45 μm) was used. The elution solvent used was 4% aqueous phosphoric acid (solution A) and acetonitrile (solution B). The column was equilibrated with 90% solution A and 10% solution B, 10 μl of sample was added simultaneously with linear increase in the proportion of solution B to reach 70% solution A and 30% solution B after 40 minutes. The flow rate of the solution was 1 ml/min, the column temperature was 40° C., and the column used was a COSMOSil, ODS-C18 by NAKARAI. The detection was performed by measurement of the absorbance at 530 nm.

In order to determine the molecular type of the pigment skeleton, hydrochloric acid was added to the extract to create acidity, heating was performed at 100° C. for 60 minutes for hydrolysis to remove the sugar chains, and analysis was carried out by HPLC. The elution solvent was at a fixed concentration of 83% solution A and 17% solution B.

When an extract from stolons of Tottori Z. *matrella* was analyzed by HPLC on Nov. 10, 1997, there were 2 main peaks at 16.930 min. and 20.750 min. (FIG. 1-971110).

Figure 2:
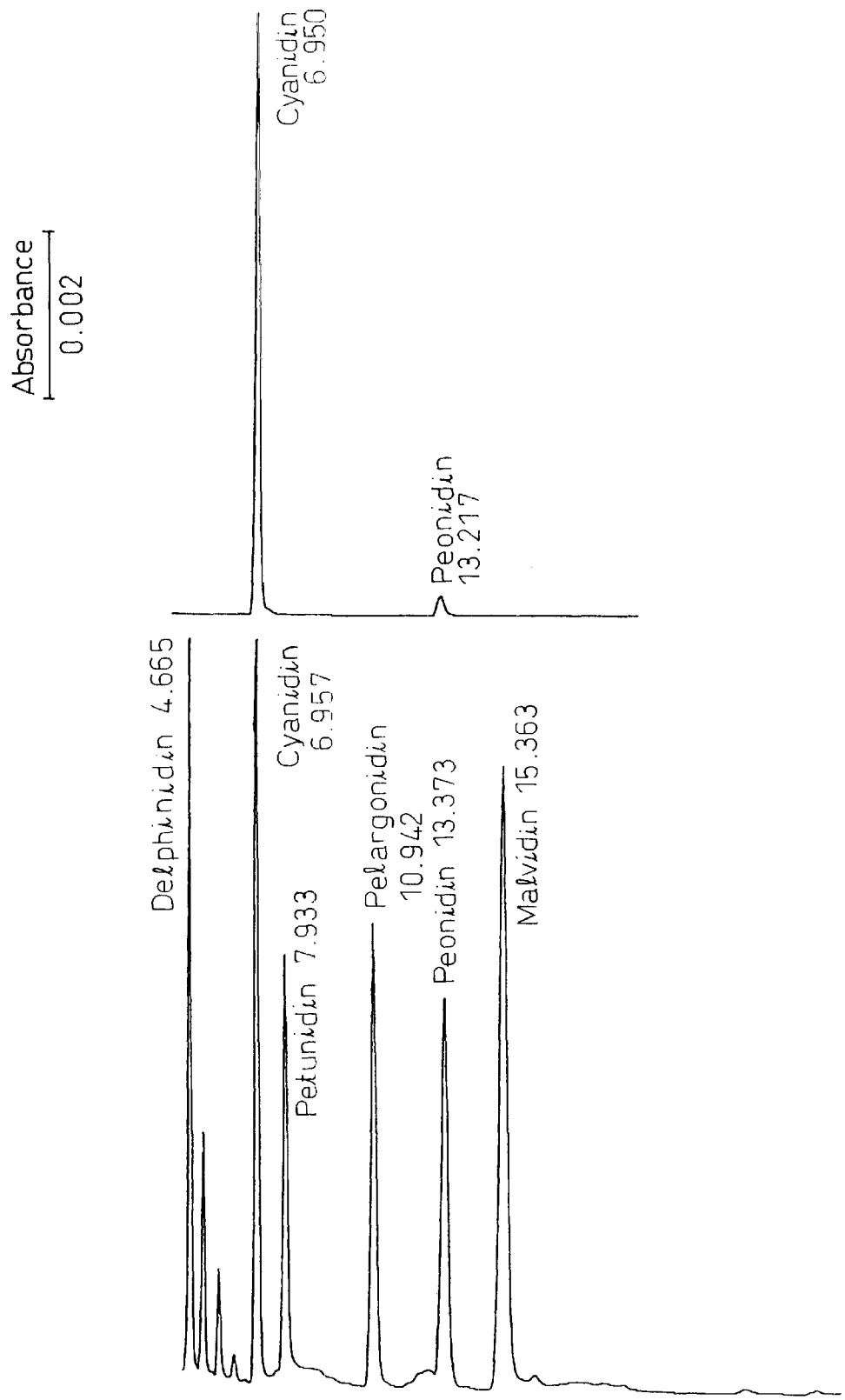
FIG. 2 shows HPLC analysis of anthocyanin hydrolysates in Tottori Z. matrella at top, and analysis of a standard substance under the same conditions at bottom.

When the sample was hydrolyzed and analyzed by HPLC to identify the aglycons of the anthocyanin molecules, a single main peak appeared at the position of 6.950 min., and a small peak appeared at 13.217 min. (FIG. 2).

Based on the retention time of the standard substance, the main peak was believed to be cyanidin and the small peak peonidin, and the two main peaks of FIG. 1-971110 were both concluded to be anthocyanins with different sugar chains on their cyanidin skeletons.

Tottori Z. *matrella* transplanted at the research field at 535 Hamakata, Hofu City from November, 1997 to February, 1998 was sampled each month and analyzed (FIG. 1).

The results showed peaks at 16.930 min. and 20.750 min. for the November sample, as mentioned above, but the peak at 16.930 min. gradually decreased becoming a small peak by the end of December. A major peak took its place at 28.052 min. by the end of January, and was maintained until the end of February. The other main peak in November at 20.750 min. was maintained throughout the measuring period though at varying heights. It was thus demonstrated that the stolons of Tottori Z. *matrella* are red throughout the year, but that the molecular composition is not constant but changes with the change in seasons.

Figure 3:
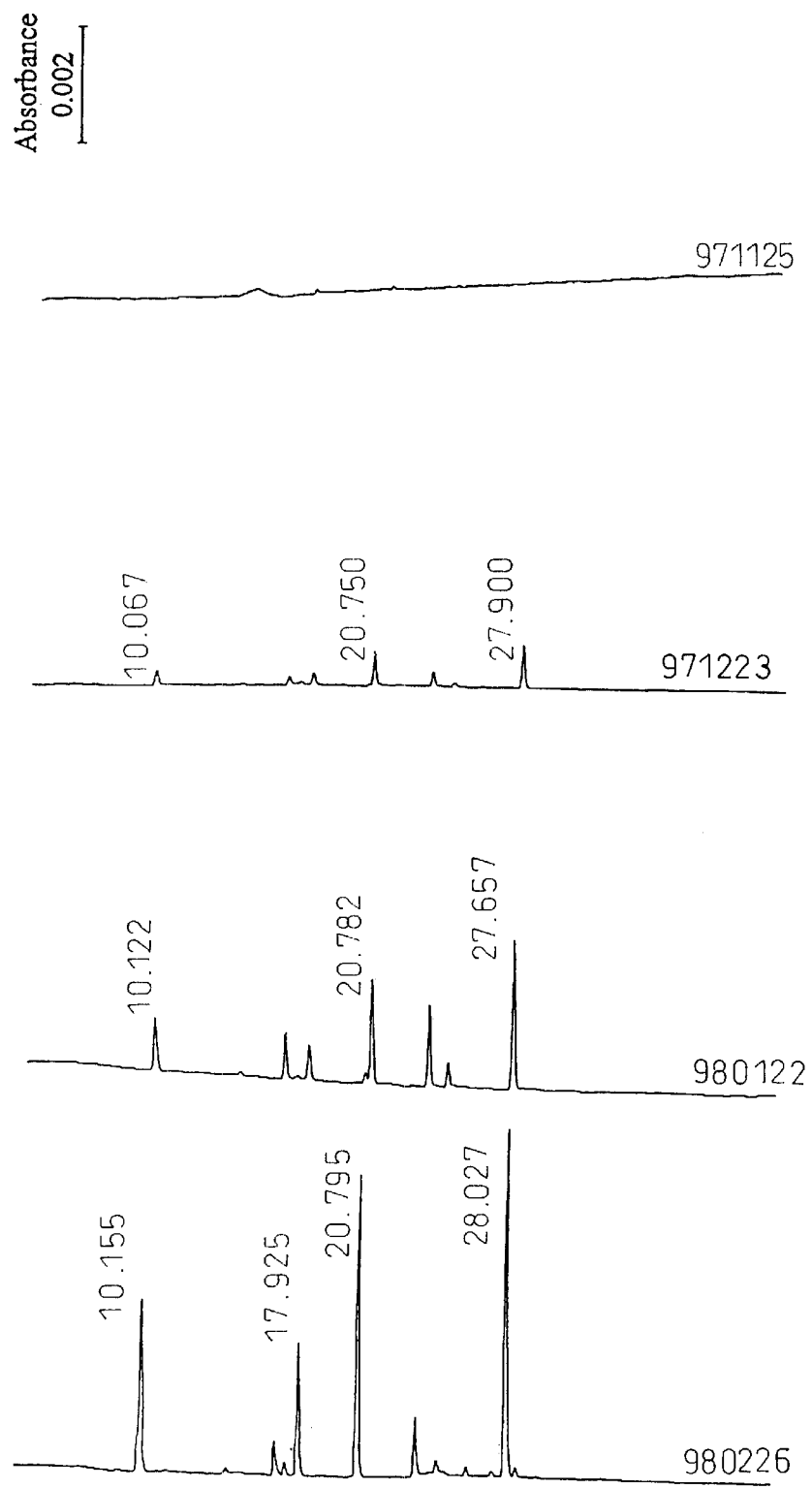
FIG. 3 shows changes in the anthocyanin composition of leaf blades of Tottori Z. matrella for Nov. 25, 1997, Dec. 23, 1997, Jan. 22, 1998 and Feb. 26, 1998 in order from top to bottom.

Tottori Z. *matrella* leaves are green in summer, and almost no anthocyanins are detected even when analysis is made at the end of November (FIG. 3). However, anthocyanin colored leaves exhibit a composition very similar to the anthocyanin composition of stolons composed mainly of anthocyanins at 20.795 min. and 28.027 min, that are seen with stolons in February.

The composition of anthocyanins produced in stolons of Tottori Z. *matrella* (*Zoysia matrella*) changes with changes in temperature or sunshine, and while the pigment reaches maximum accumulation in early winter, eventually reaching the anthocyanin composition of leaves and stolons in the cold season. The winter anthocyanin composition changes as the anthocyanins in the leaves disappear with warming weather, and the stolons exhibit a warm season anthocyanin composition. The anthocyanin composition of Tottori Z. *matrella* traverses this cycle throughout the year.

Figure 4:
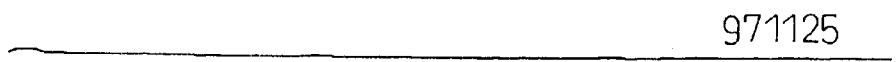
FIG. 4 shows changes in the anthocyanin composition of leaf blades of TK-XG1 for Nov. 25, 1997, Dec. 23, 1997, Jan. 22, 1998 and Feb. 26, 1998 in order from top to bottom.
Figure 4:
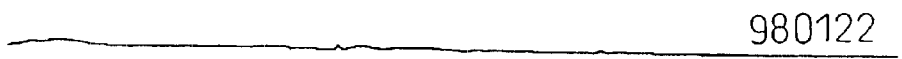
Figure 4:
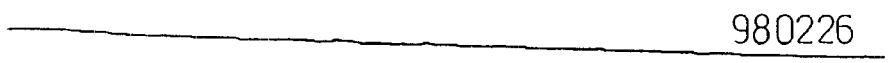
Figure 5:
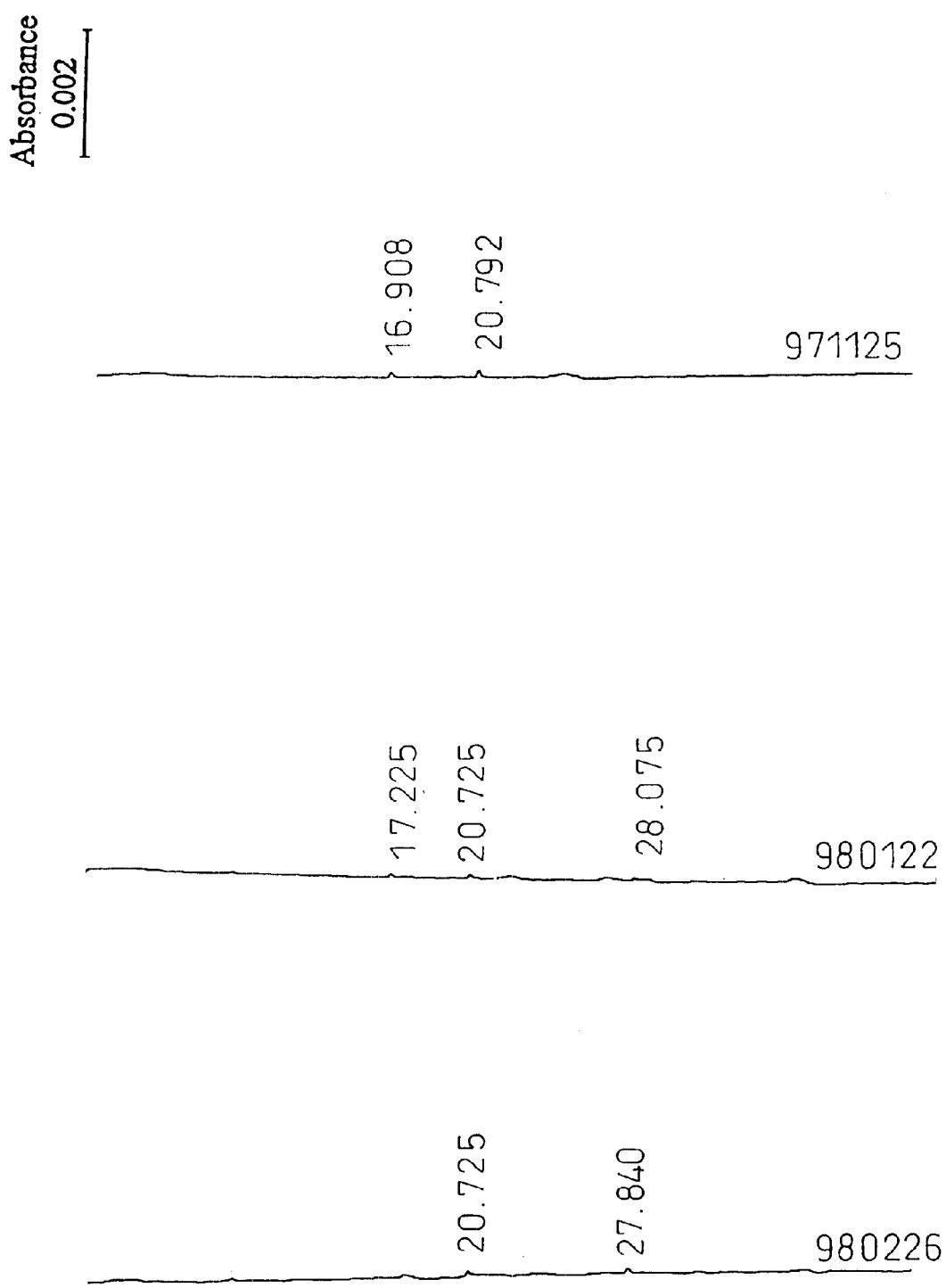
FIG. 5 shows changes in the anthocyanin composition of leaf blades of TK-XG1 for Nov. 25, 1997, Dec. 23, 1997, Jan. 22, 1998 and Feb. 26, 1998 in order from top to bottom.

The leaves of the TK-XG1 of the invention produced no anthocyanins when measured from November, 1997 through February, 1998 (FIG. 4). Two trace peaks were detected in the stolons at 16.908 and 20.792 on November 25, while only trace peaks were detected at 17.225, 20.725 and 28.075 on January 22, and at 20.725 and 27.840 on February 26 (FIG. 5).

Thus, Tottori Z. *matrella* accumulates the red pigment anthocyanins in the leaves in winter, whereas the new variety TK-XG1 accumulates no anthocyanins in the leaves during winter. Moreover, anthocyanins are produced in the stolons in only trace amounts, and may therefore be considered to contain substantially no anthocyanins. Outwardly, TK-XG1 exhibited no anthocyanin coloring at any part or in any season.

Determination of Anthocyanin Molecular Structures

TK-XG1 contains only trace amounts of molecules at 17 minutes and 20 minutes among the anthocyanin molecules typically appearing in Manilagrass and, therefore, it possesses, as a major feature, a relatively substantial absence of anthocyanins. In order to elucidate the molecular structures of the anthocyanins, Tottori Z. *matrella* was used to determine the structures of anthocyanins in Manilagrass.

The molecular structures were determined by the method of co-chromatography, and as a result it was found that the principal anthocyanins in Manilagrass are cyanidin 3-glucoside (Cy3G) at 10 min., cyanidin 3-malonylglucoside (Cy3MG) at 17 min., cyanidin 3-dimalonylglucoside (Cy3DMG) at 20 min. and cyanidin 3-polymalonylglucoside (Cy3PMG) at 28 min.

Chlorophyll Concentration in Winter

The changes in chlorophyll concentration in TK-XG1 and the Tottori *Z. matrella* parental strain were measured between September, 1997 and March, 1998 (see Table 6).

TABLE 6

Chlorophyll contents in Tottori *Z. matrella* and TK-XG1

| Sampling date Yr Mon Day | *Zoysia matrella* (Tottori *Z. matrella*) | | | *Zoysia matrella* (TK-XG1) | | |
|---|---|---|---|---|---|---|
| | Chl a (mg/g) | Chl b (mg/g) | Total (mg/g) | Chl a (mg/g) | Chl b (mg/g) | Total (mg/g) |
| 97 09 29 | 1.11 | 0.44 | 1.55 | 1.48 | 0.60 | 2.09 |
| 97 10 13 | 1.16 | 0.42 | 1.57 | 1.83 | 0.57 | 2.40 |
| 97 10 29 | 0.98 | 0.35 | 1.37 | 1.85 | 0.59 | 2.43 |
| 97 12 10 | 0.91 | 0.32 | 1.23 | 1.32 | 0.49 | 1.81 |
| 98 01 27 | 1.06 | 0.38 | 1.42 | 1.25 | 0.42 | 1.68 |
| 98 02 12 | 0.82 | 0.25 | 1.07 | 1.04 | 0.32 | 1.37 |
| 98 03 24 | 1.15 | 0.41 | 1.56 | 1.35 | 0.44 | 1.79 |

The chlorophyll was extracted from the leaf blades with 80% acetone, the absorbance was measured at 645 nm and 663 nm, and the content was calculated by the Arnon formula (Arnon, 1949, Plant Physiology, 24, 1–15). The Tottori *Z. matrella* suffered winter withering in winter, with a content of less than 1% in the living leaves. Since only the living leaves were selected for use, excluding the withered leaves, the Tottori *Z. matrella* had a higher value than expected for the visual sensation appearance of total winter withering, but it still had a significantly lower chlorophyll content in winter than TK-XG1.

DNA analysis of TK-XG1 by RAPD Method

Figure 7:
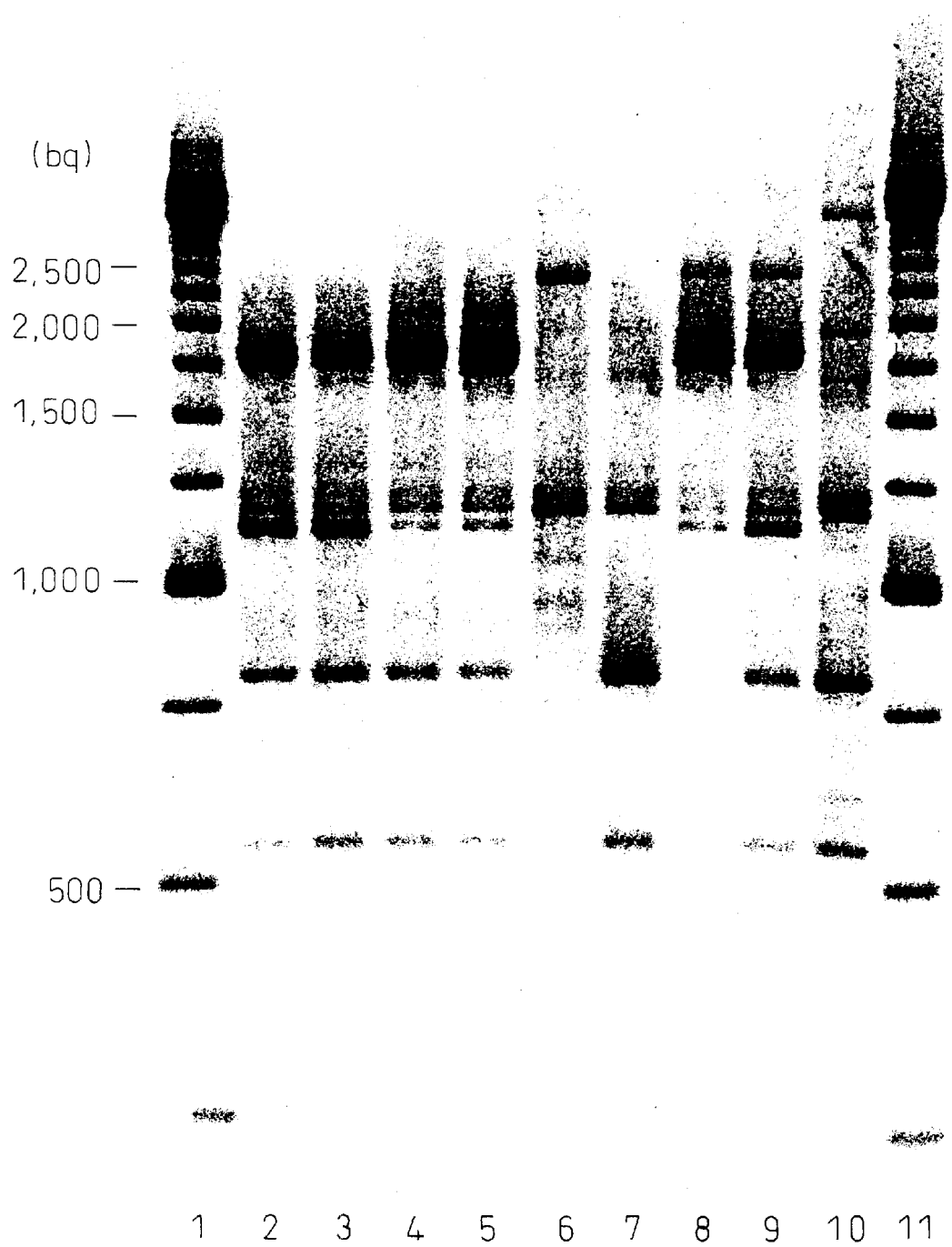
FIG. 7 is a gel electrophoresis pattern used to distinguish varieties by the RAPD method using primer B.
Figure 8:
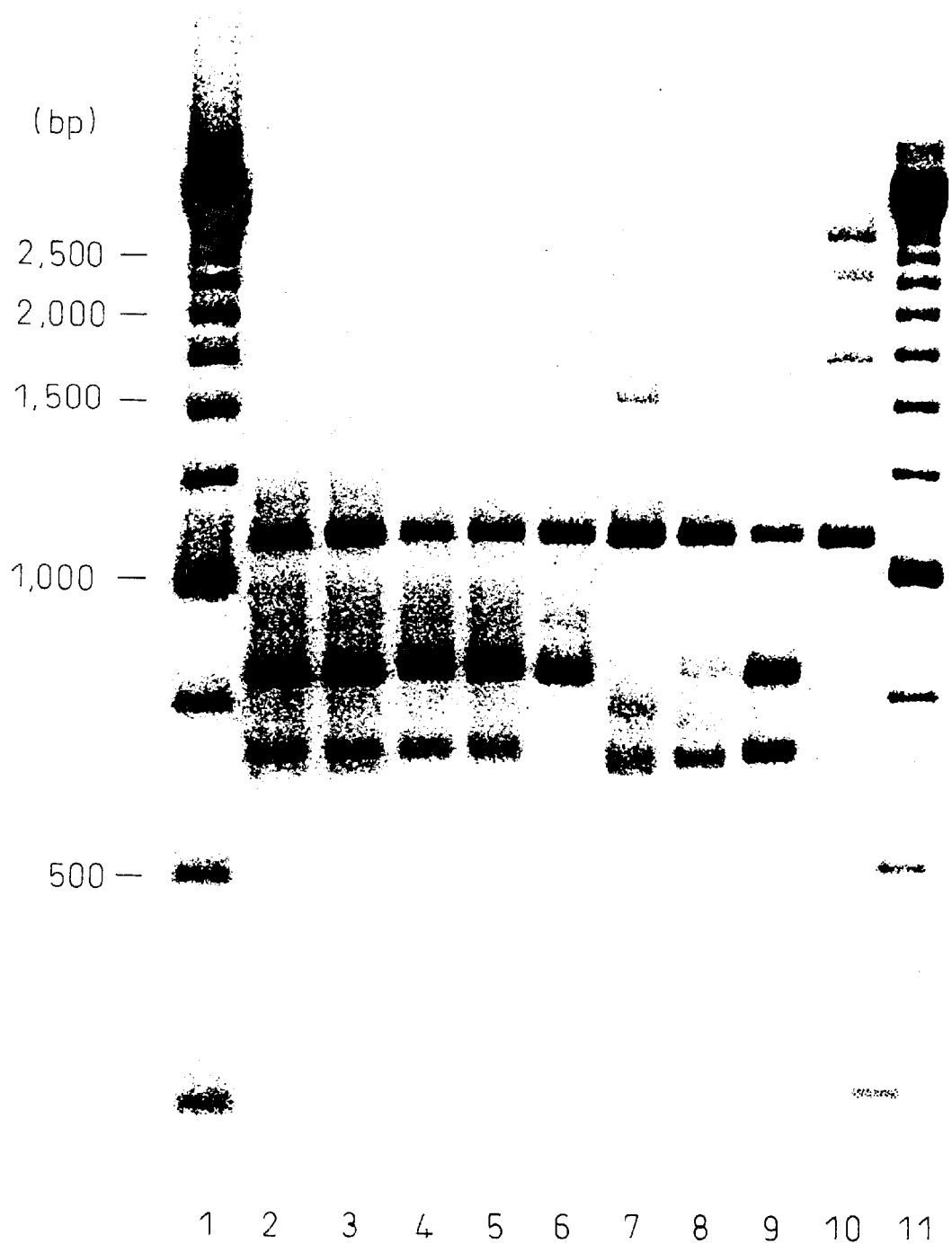
FIG. 8 is a gel electrophoresis pattern used to distinguish varieties by the RAPD method using primer C.
Figure 9:
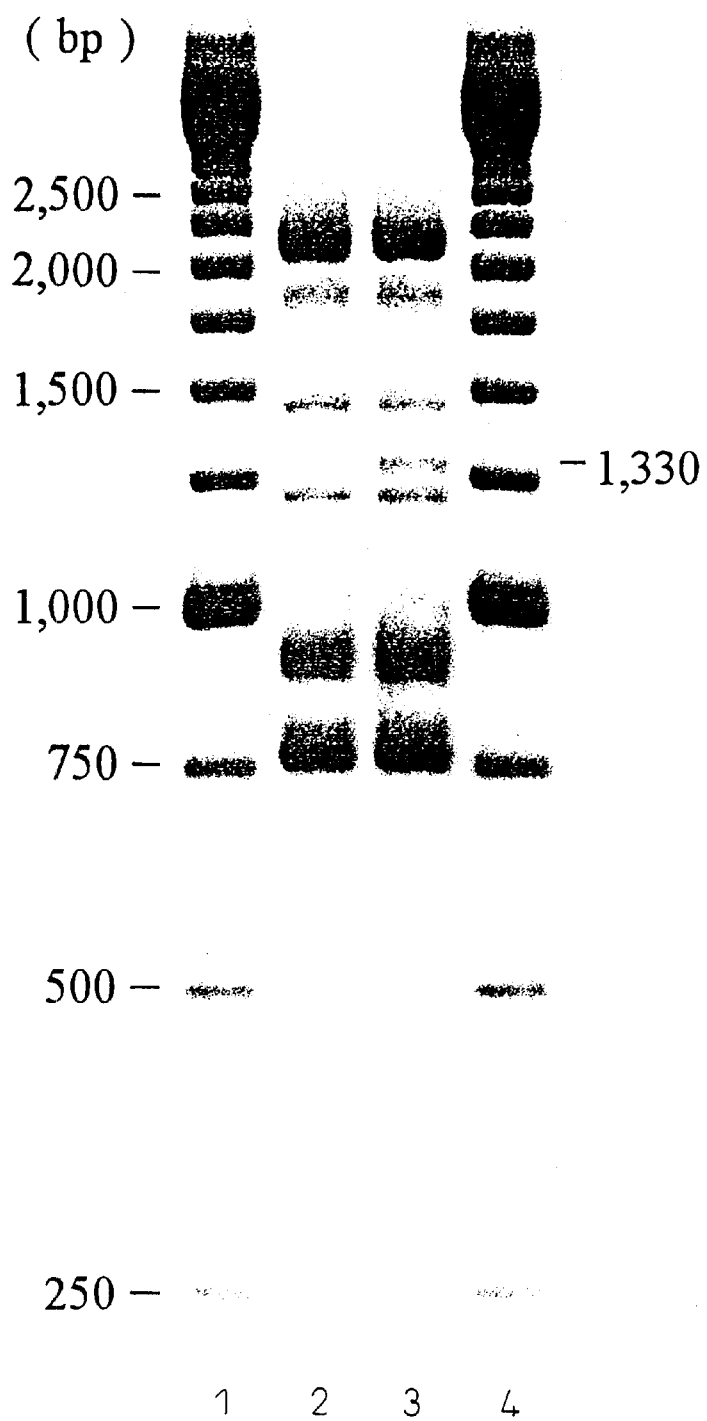
FIG. 9 is a gel electrophoresis pattern used to distinguish varieties by the RAPD method using primer D.
Figure 10:
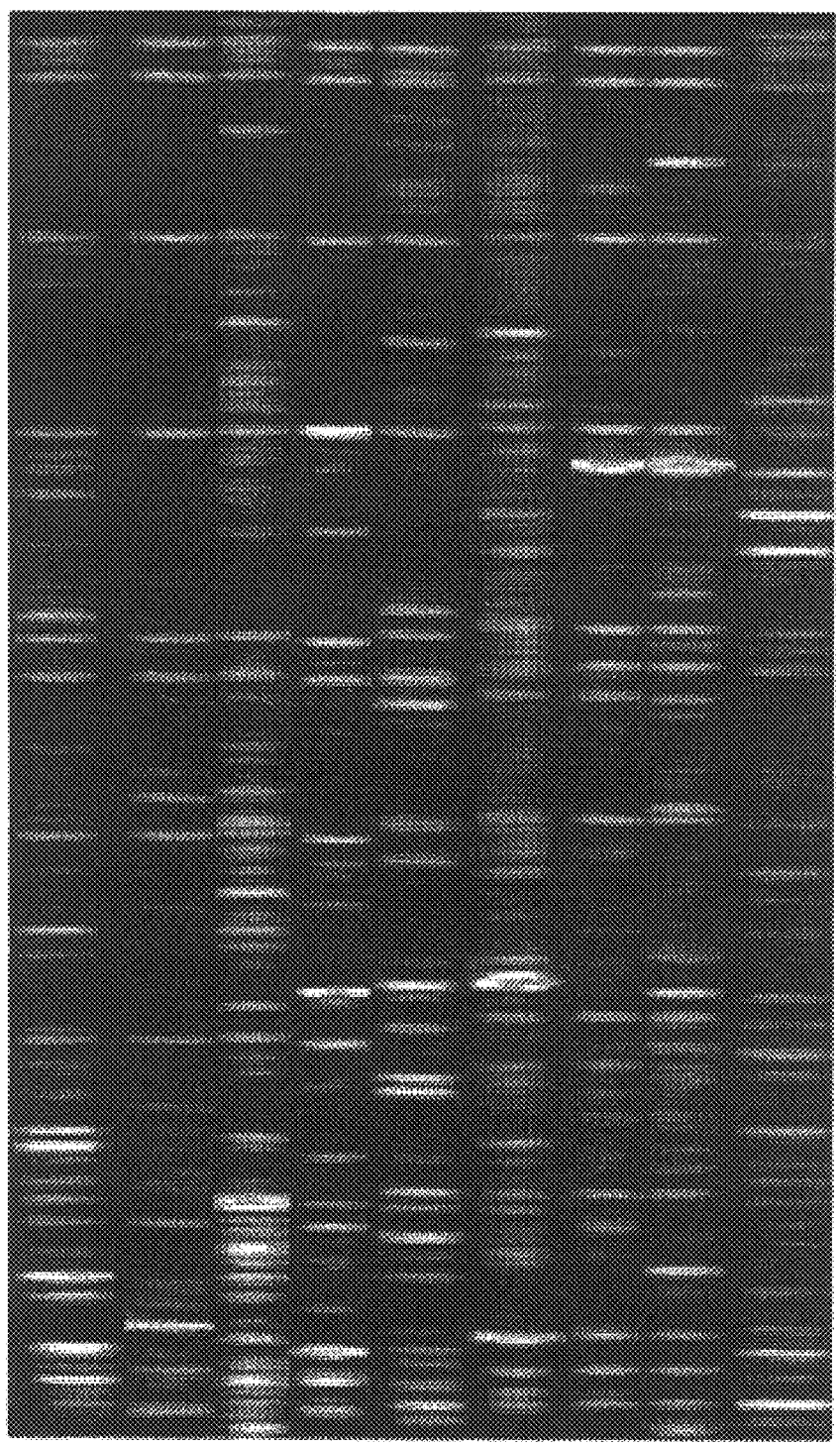
FIG. 10 is a gel electrophoresis pattern for TK-XG1 by the AFLP method using a combination of 9 primers.
Figure 11A:
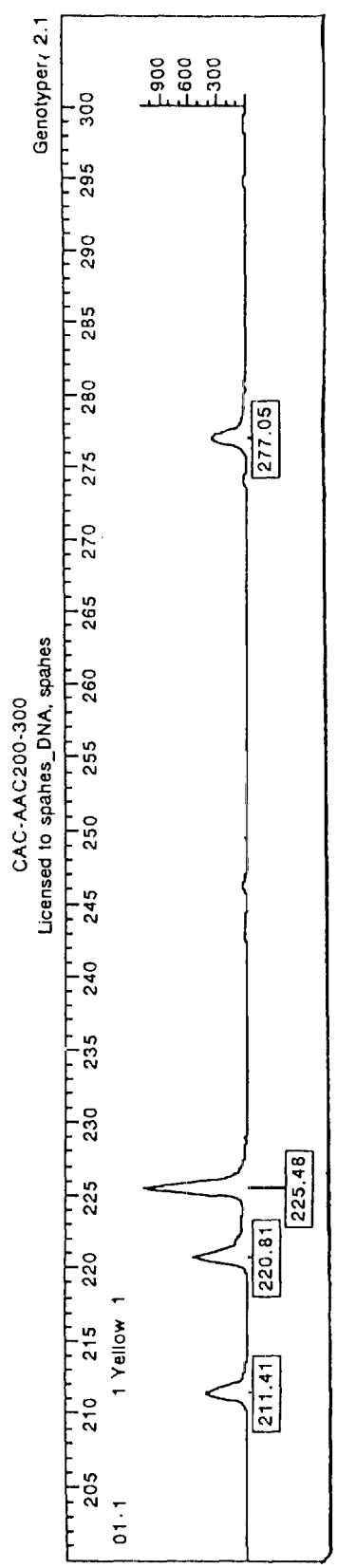
FIGS. 11a to 11i are electropherograms used to analyze signals detected with analysis software after gel electrophoresis of TK-XG1 by the AFLD method using a combination of 9 primers.
Figure 11B:
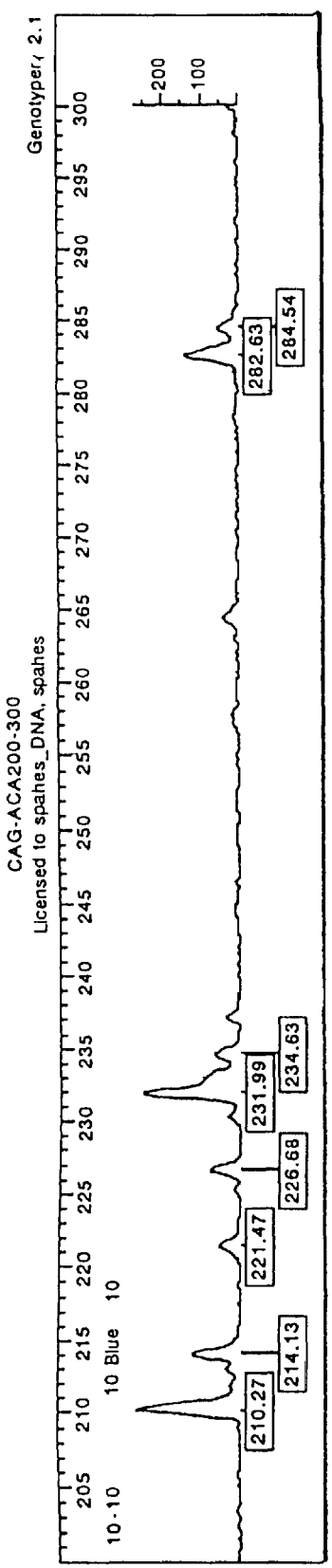
Figure 11C:
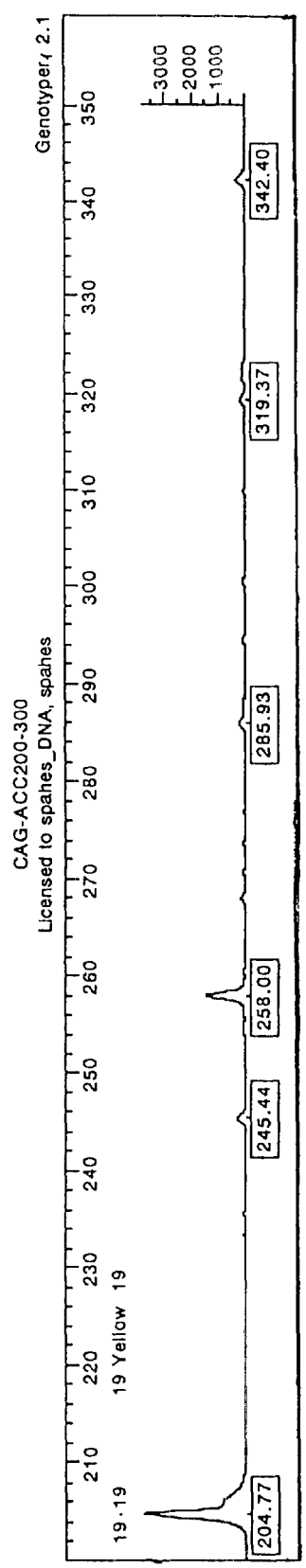
Figure 11D:
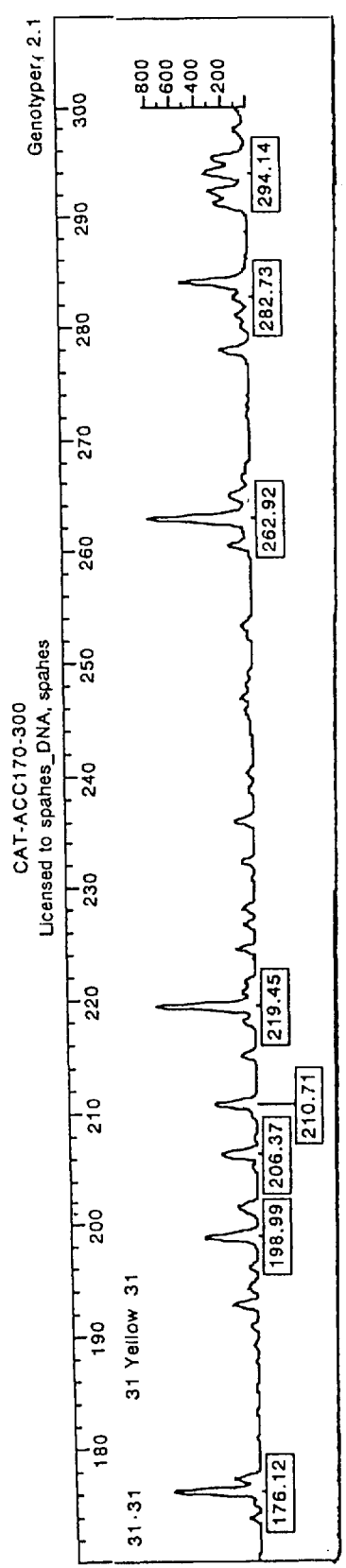
Figure 11E:
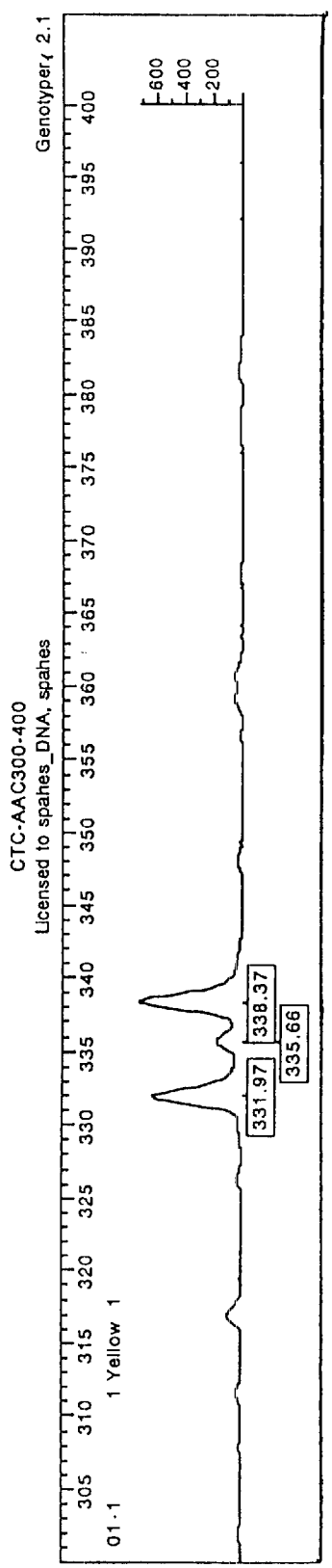
Figure 11F:
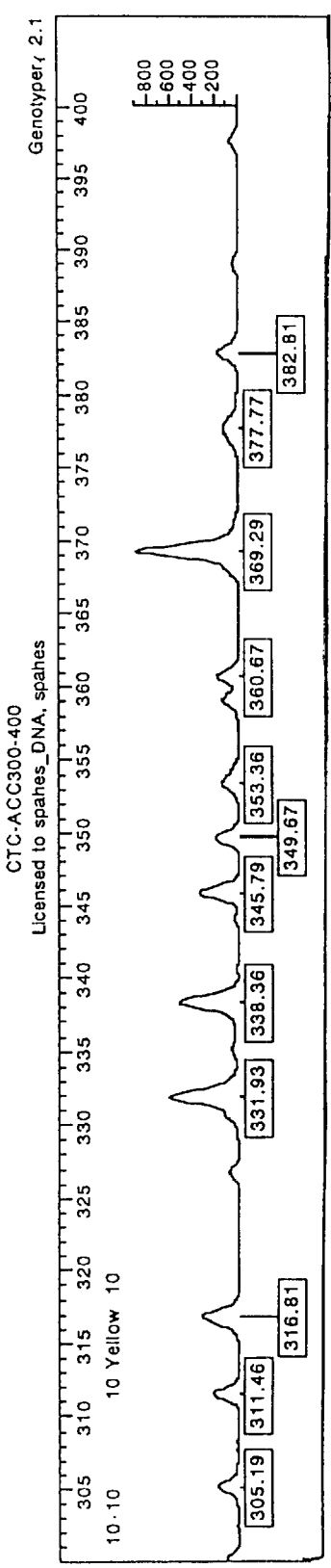
Figure 11G:
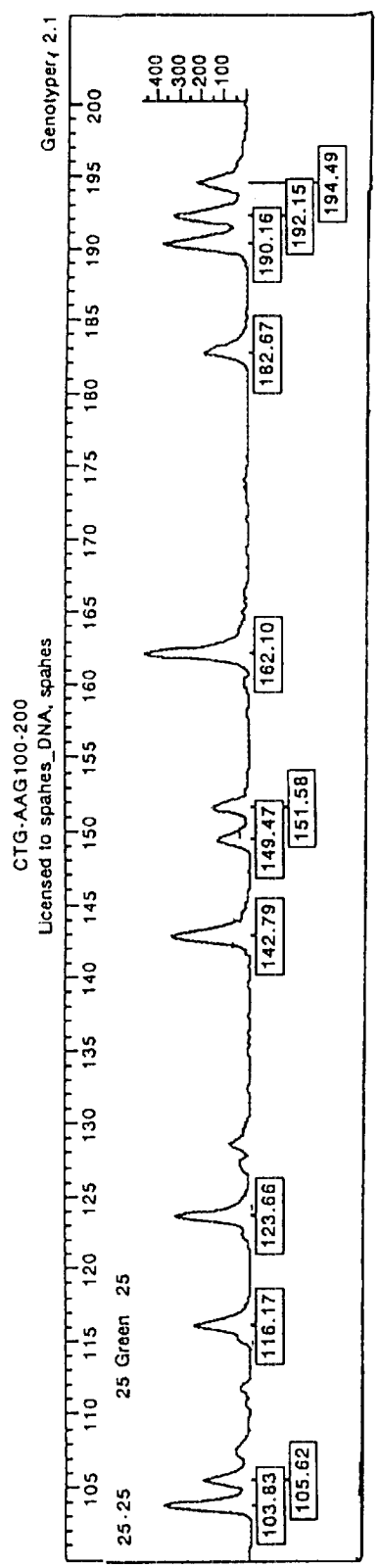
Figure 11H:
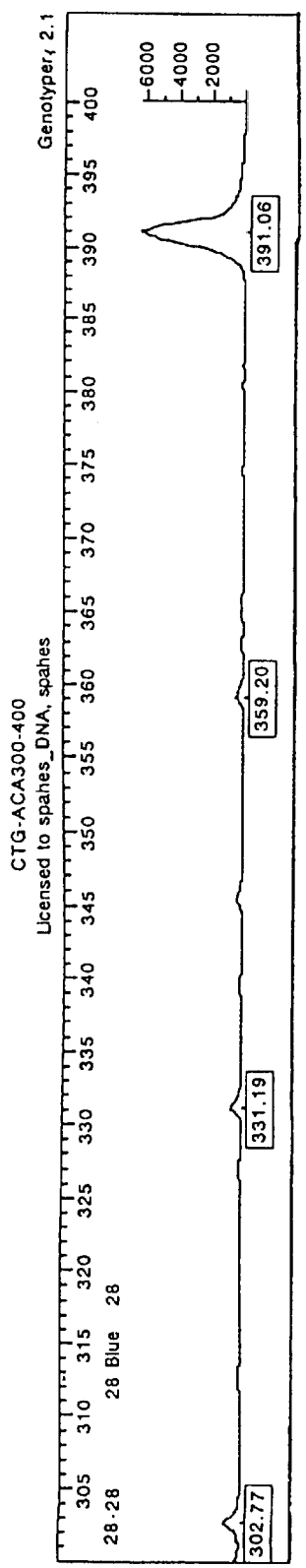
Figure 11I:
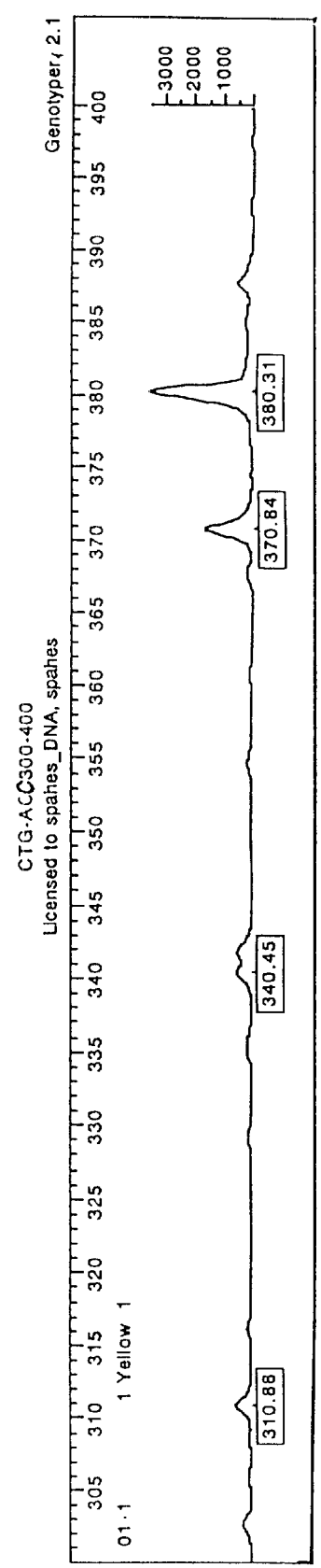

In order to clearly elucidate the differences between TK-XG1 and other varieties, analysis was performed by the RAPD (Random Amplified Polymorphic DNA) method (see FIGS. 6–10). Nine varieties were used, TK-XG1 and eight controls: Tottori *Z. matrella*, winterfield (*Zoysia matrella*, registered variety in Japan), Wintercarpet (*Zoysia matrella*, registered variety in Japan), Victoria (also known as Preciousgreen. *Zoysia japonica*, plant patented in U.S.), Miyako (*Zoysia japonica*×*Zoysia matrella* or *Zoysia japonica*, registered variety in Japan), Meyer (*Zoysia japonica*, registered variety in U.S.), Emerald (*Zoysia japonica*×*Zoysia tenuifolia*, registered variety in U.S.) and El Toro (*Zoysia japonica*, plant patented in U.S.), were cultivated under the same conditions as the research field at Kaisui Chemical Industry Co., Ltd., and the same volume of leaves were sampled on the same day and the DNA extracted by the CTAB (Cetyltrimethylammonium bromide) method. The DNA was used as a template for PCR (Polymerase Chain Reaction) using primers with the sequences given below. The reaction conditions were 2 minutes at 94° C. for pre-amplification heat denaturation, 30 seconds at 94° C. for denaturation for the amplification cycle, 30 seconds at 34° C. for annealing and 2 minutes at 68° C. for extension. This cycle was repeated 45 times for reaction, followed by a final extension for 5 minutes at 68° C. A 2% agarose gel was used for electrophoresis. The primers for the photographs shown as data were the four primers with the following sequences Primer A: TTCCGTAATCAC (FIG. 6)
Primer B: AGAGGTGTAAAT (FIG. 7)
Primer C: TTGCATAATCGT (FIG. 8)
Primer D: CCTTGGAACTCG (FIG. 9)

Figure 6:
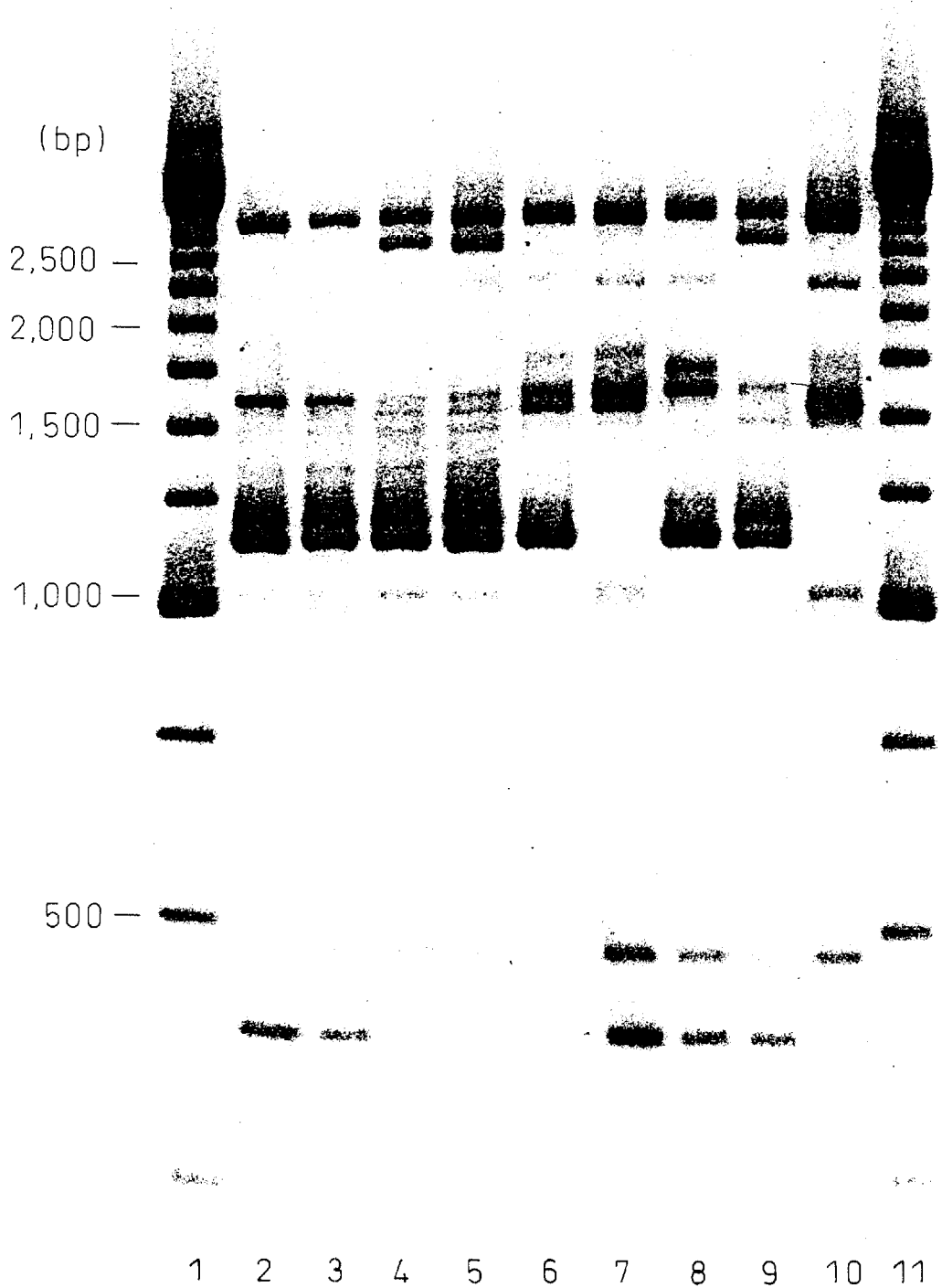
FIG. 6 is a gel electrophoresis pattern used to distinguish varieties by the RAPD method using primer A.

TK-XG1, Tottori *Z. matrella* and the other varieties can be distinguished by comparison of the electrophoretic images of their PCR amplification products using primers A, B and C, for example (see FIGS. 6, 7, 8). The Tottori *Z. matrella* produces a band at 1330 bp by amplification with primer D, and since this is absent with TK-XG1 this can be used to distinguish the two varieties (see FIG. 9).

The base sequences of the primers used for PCR amplification in FIGS. 6 to 9 have been given above. Lanes 1) and 11) in FIGS. 6, 7 and 8 are molecular weight markers at 250 bp spacings, and the 1000 bp bands are indicated by an arrow. The other lanes are 2) TK-XG1, 3) Tottori *Z. matrella*, 4) Wintercarpet, 5) Winterfield, 6) Victoria, 7) Miyako, 8) Meyer, 9) Emerald and 10) El Toro. Lanes 1) and 4) in FIG. 9 are molecular weight markers, lane 2) is TK-XG1 and lane 3) is Tottori *Z. matrella*.

DNA Analysis of TK-XG1 by AFLP Method

In order to clearly elucidate the differences between TK-XG1 and other varieties, analysis was performed by the AFLP (Amplified Fragment Length Polymorphism) method. Leaves were collected from TK-XG1 cultivated at the research field at Kaisui Chemical Industry Co., Ltd., and the DNA was extracted by the CTAB (Cetyltrimethylammonium bromide) method. After cutting the DNA with two different restriction endonucleases EcoRI (6-base recognizing enzyme) and MseI (4-base recognizing enzyme), a double-stranded adapter was linked to both ends of the DNA fragment which was then subjected to Preselective PCR (Polymerase Chain Reaction: preselective amplification) first and then a preselective primer was used to add one additional base downstream from the restriction endonuclease site and only the matching bases of the restriction endonuclease fragment were selectively amplified. The reaction conditions were one cycle of 2 minutes at 72° C. for pre-amplification heat denaturation, followed by 20 cycles of 20 seconds at 94° C. for denaturation for the amplification cycle, 30 seconds at 56° C. for annealing and 2 minutes at 72° C. for extension. A 1.2% agarose gel was used for electrophoresis to identify the PCR product. A fluorescent dye-labeled selective primer was then used for a second PCR (selective amplification) reaction. The reaction conditions are shown in Table 7. A mixture of the second PCR product, loading dye and ROX500 Size Standard was used for the electrophoresis sample. A DNA sequencer (ABI PRISM377 DNA Sequencer) was used for fractionation with 6% polyacrylamide gel electrophoresis (FIG. 10), after which analysis software (ABI PRISM Gene Scan Analysis) was used for analysis of the detected signal on an electropherogram (FIG. 11*a* to FIG. 11*i*). The experiment was repeated 3 times.

TABLE 7

Reaction conditions for second PCR by AFLP method

| 94° C. | 2 min. | | | | | | |
|---|---|---|---|---|---|---|---|
| 94° C. | 20 sec. | 66° C. | 30 sec. | 72° C. | 2 min. | 1 cycle |
| 94° C. | 20 sec. | 65° C. | 30 sec. | 72° C. | 2 min. | 1 cycle |
| 94° C. | 20 sec. | 64° C. | 30 sec | 72° C. | 2 min. | 1 cycle |

TABLE 7-continued

Reaction conditions for second PCR by AFLP method

| | | | | | | |
|---|---|---|---|---|---|---|
| 94° C. | 20 sec. | 63° C. | 30 sec. | 72° C. | 2 min. | 1 cycle |
| 94° C. | 20 sec. | 62° C. | 30 sec. | 72° C. | 2 min. | 1 cycle |
| 94° C. | 20 sec. | 61° C. | 30 sec. | 72° C. | 2 min. | 1 cycle |
| 94° C. | 20 sec. | 60° C. | 30 sec. | 72° C. | 2 min. | 1 cycle |
| 94° C. | 20 sec. | 59° C. | 30 sec. | 72° C. | 2 min. | 1 cycle |
| 94° C. | 20 sec. | 58° C. | 30 sec. | 72° C. | 2 min. | 1 cycle |
| 94° C. | 20 sec. | 57° C. | 30 sec. | 72° C. | 2 min. | 1 cycle |
| 94° C. | 20 sec. | 56° C. | 30 sec. | 72° C. | 2 min. | 20 cycles |
| 60° C. | 30 sec. | | | | | |
| Stored at 4° C. | | | | | | |

Confirming Fixation by Large-scale Culturing with Multiple Shoots

Culturing of the growth points of TK-XG1 in Murashige-Skoog medium containing 0.02 mg/l NAA and 0.2 mg/l BA produces multiple shoots (Japanese Unexamined Patent Publication No. 7-313008). The multiple shoots are aggregates of buds, and culturing of a single multiple shoot in a large-sized vessel under the same conditions results in growth to about 100 multiple shoots within two months. The multiple shoots can produce shoots with roots to yield about 10,000 young plants. When these were transferred to a research field and raised, none of the plants showed a transformation to the TK-XG1 character. That is, the character of each apical bud was stable even when grown to 10,000 plants, and the character was even stable with growth at the field from September, 1997 and later, or at least the useful character described above was preserved with vegetative propagation.

The present inventors therefore designed production of "Manilagrass that retains green leaves in winter", and as the method used to realize this goal, highly differentiated shoot primordium cultured cells capable of reproduction through callus formation were prepared and irradiated with, for example, ultraviolet rays or soft X-rays to introduce the necessary mutations, and a special cell selection method was adopted and carried out whereby the green colored cells were selected, to obtain the originally targeted new turfgrass variety.

EXAMPLE 2

Observation of Retained Green Leaves of TK-XG1 in Chugoku area Cold District A test was conducted to evaluate TK-XG1 and Tottori Z. matrella at the Hiroshima Prefectural University Agricultural Research station (562 Nanatsukahara, Shobara City, Hiroshima Prefecture, Japan) during the period from late November, 1998 to early March, 1999. During this period, the TK-XG1 clearly retained its green leaves, but the Tottori Z. matrella produced anthocyanin colored leaves and withered leaf by mid December and could not retain its green color (Table 8).

TABLE 8

Observation of retained green color of TK-31 XG1 in Chugoku area cold district (Hiroshima Prefectural University: 562 Nanatsukahara, Shobara City, Hiroshima Prefecture)

| | Date | | | |
|---|---|---|---|---|
| Variety | Nov. 24, 1998 | Dec. 9, 1998 | Dec. 23, 1998 | Jan. 28, 1999 |
| TK-XG1 | 5 | 5 | 4 | 4 |
| Tottori Z. matrella | 5 | 3 | 2 | 2–1 |

5 - Totally green living leaves
4 - Reduced green color, with some withered leaves
3 - Partially anthocyanin colored or purplish red leaves
2 - Totally anthocyanin colored or purplish red leaves
1 - Withered leaves The weather conditions at the research station during the test period are shown in Table 9.

TABLE 9

Weather conditions from Dec. 11, 1998 to Mar. 10, 1999 in Chugoku area cold district (Hiroshima Prefectural University: 562 Nanatsukahara, Shobara City, Hiroshima Prefecture)

| Yr.Mon.Day | | | Mean temperature (° C.) | Highest temperature (° C.) | Lowest temperature (° C.) | Sunshine time (hr) |
|---|---|---|---|---|---|---|
| 1998 | 12 | 11 | 1.9 | 6.3 | −1.6 | 2.6 |
| | | 12 | 3.2 | 9.8 | −1.2 | 8.5 |
| | | 13 | 2.6 | 12.1 | −5.1 | 6.7 |
| | | 14 | 4.8 | 11.4 | −1.7 | 4.8 |
| | | 15 | 6.5 | 9.7 | 1.9 | 5.7 |
| | | 16 | 5.2 | 11.7 | 0.4 | 6.7 |
| | | 17 | 4.6 | 13.8 | −2.1 | 6.9 |
| | | 18 | 3.5 | 12.5 | −3.2 | 7.2 |
| | | 19 | 4.0 | 13.6 | −2.2 | 4.9 |
| | | 20 | 6.2 | 11.6 | 0.2 | 7.8 |
| Mid ten days of the month | | | 4.3 | 13.8 | −5.1 | 61.8 |
| | | 21 | 2.6 | 10.8 | −3.2 | 7.7 |
| | | 22 | 3.8 | 13.6 | −3.9 | 7.9 |
| | | 23 | 4.0 | 11.8 | −2.4 | 5.3 |
| | | 24 | 4.5 | 8.4 | 1.2 | 4.8 |
| | | 25 | 2.9 | 9.7 | −2.6 | 8.6 |
| | | 26 | 4.1 | 11.3 | 0.0 | 5.4 |
| | | 27 | 2.4 | 6.5 | −2.0 | 0.7 |
| | | 28 | 5.0 | 11.3 | 0.4 | 4.9 |
| | | 29 | 3.4 | 10.1 | −2.2 | 3.5 |
| | | 30 | 3.2 | 7.7 | −0.1 | 7.3 |
| Late ten days of the month | | | 3.6 | 13.6 | −3.9 | 56.1 |
| | 12 | 31 | 1.3 | 5.8 | −0.8 | 3.6 |
| 1999 | 1 | 1 | 0.8 | 3.8 | −1.2 | 1.4 |
| | | 2 | −0.3 | 2.8 | −2.2 | 1.2 |
| | | 3 | 1.7 | 7.8 | −1.8 | 3.1 |
| | | 4 | 1.6 | 8.9 | −1.9 | 5.2 |
| | | 5 | 1.1 | 11.0 | −5.0 | 7.1 |
| | | 6 | 2.7 | 9.4 | −4.4 | 5.6 |
| | | 7 | 1.8 | 5.7 | −3.9 | 2.9 |
| | | 8 | −4.4 | −3.1 | −5.2 | 3.9 |
| | | 9 | −3.9 | −1.1 | −6.3 | 4.6 |
| Early ten days of the month | | | 0.2 | 11.0 | −6.3 | 38.6 |
| | | 10 | −1.5 | 0.9 | −4.2 | 4.1 |
| | | 11 | 0.1 | 3.2 | −1.3 | 3.7 |
| | | 12 | −0.7 | 2.5 | −2.5 | 5.4 |
| | | 13 | −0.5 | 4.0 | −5.9 | 5.8 |
| | | 14 | 1.1 | 7.0 | −3.4 | 7.1 |
| | | 15 | −0.4 | 2.9 | −3.2 | 2.1 |

TABLE 9-continued

Weather conditions from Dec. 11, 1998 to
Mar. 10, 1999 in Chugoku area cold district
(Hiroshima Prefectural University: 562
Nanatsukahara, Shobara City, Hiroshima Prefecture)

| Yr.Mon.Day | | | Mean temperature (° C.) | Highest temperature (° C.) | Lowest temperature (° C.) | Sunshine time (hr) |
|---|---|---|---|---|---|---|
| | | 16 | −0.4 | 5.0 | −5.1 | 4.4 |
| | | 17 | 1.6 | 7.1 | −2.9 | 8.9 |
| | | 18 | 1.0 | 9.6 | −4.5 | 5.4 |
| | | 19 | 1.7 | 3.9 | −1.2 | 0.0 |
| Mid ten days of the month | | | 0.2 | 9.6 | −5.9 | 46.9 |
| | | 20 | 2.4 | 7.0 | 0.1 | 3.6 |
| | | 21 | 0.6 | 5.5 | −3.6 | 6.2 |
| | | 22 | 0.4 | 9.4 | −7.2 | 8.6 |
| | | 23 | 4.0 | 9.9 | −2.2 | 4.5 |
| | | 24 | 5.0 | 10.5 | 0.0 | 3.3 |
| | | 25 | 3.8 | 10.2 | −1.2 | 2.1 |
| | | 26 | 3.9 | 8.7 | −3.0 | 8.1 |
| | | 27 | 1.8 | 9.0 | −5.1 | 5.6 |
| | | 28 | 2.1 | 7.4 | −3.6 | 5.8 |
| | | 29 | −1.1 | 2.9 | −3.8 | 4.0 |
| Late ten days of the month | | | 2.3 | 10.5 | −7.2 | 51.8 |
| 1999 | 1 | 30 | −0.3 | 5.0 | −4.0 | 6.3 |
| | | 31 | 1.3 | 9.5 | −4.9 | 8.5 |
| | 2 | 1 | 3.3 | 8.5 | −0.2 | 1.8 |
| | | 2 | −0.2 | 4.5 | −2.8 | 2.7 |
| | | 3 | −4.7 | −2.3 | −7.4 | 3.7 |
| | | 4 | −4.6 | 2.0 | −10.7 | 7.2 |
| | | 5 | −1.8 | 1.7 | −5.1 | 4.8 |
| | | 6 | −0.8 | 5.2 | −4.9 | 7.7 |
| | | 7 | 0.5 | 8.4 | −6.3 | 9.1 |
| | | 8 | 0.9 | 9.0 | −5.7 | 6.2 |
| Early ten days of the month | | | −0.6 | 9.5 | −10.7 | 58.0 |
| | | 9 | 2.7 | 11.5 | −3.9 | 8.1 |
| | | 10 | 3.4 | 9.7 | −1.7 | 6.2 |
| | | 11 | 1.8 | 4.7 | −0.6 | 1.2 |
| | | 12 | −1.1 | 1.2 | −3.3 | 6.4 |
| | | 13 | −2.5 | −0.1 | −5.0 | 6.3 |
| | | 14 | −1.5 | 4.0 | −5.2 | 6.9 |
| | | 15 | −0.7 | 4.5 | −4.9 | 2.1 |
| | | 16 | 1.8 | 11.5 | −4.3 | 7.4 |
| | | 17 | 4.2 | 13.5 | −4.6 | 8.9 |
| | | 18 | 3.3 | 5.3 | 1.5 | 0.0 |
| Mid ten days of the month | | | 1.1 | 13.5 | −5.2 | 53.5 |
| | | 19 | 0.2 | 2.2 | −2.6 | 3.1 |
| | | 20 | −1.4 | 0.7 | −3.0 | 6.4 |
| | | 21 | −2.0 | 1.3 | −4.1 | 7.7 |
| | | 22 | −0.9 | 5.6 | −6.7 | 8.3 |
| | | 23 | 2.5 | 8.4 | −2.5 | 8.3 |
| | | 24 | 2.4 | 4.5 | −0.1 | 0.0 |
| | | 25 | 5.6 | 12.5 | 0.4 | 8.1 |
| | | 26 | 3.3 | 8.1 | −2.7 | 0.3 |
| | | 27 | 4.0 | 7.5 | −1.0 | 5.4 |
| | | 28 | 2.2 | 9.2 | −2.7 | 8.5 |
| Late ten days of the month | | | 1.6 | 12.5 | −6.7 | 56.1 |
| | 3 | 1 | 3.5 | 11.0 | −2.7 | 8.8 |
| | | 2 | 5.2 | 13.1 | −1.6 | 6.7 |
| | | 3 | 6.5 | 15.5 | −1.7 | 10.1 |
| | | 4 | 5.8 | 15.0 | −2.3 | 5.7 |
| | | 5 | 10.1 | 16.5 | 5.7 | 1.7 |
| | | 6 | 8.4 | 15.2 | 2.6 | 9.9 |
| | | 7 | 5.2 | 6.4 | 3.8 | 0.0 |
| | | 8 | 5.5 | 11.4 | 2.1 | 7.2 |
| | | 9 | 3.2 | 4.2 | 1.0 | 0.0 |
| | | 10 | 5.3 | 12.3 | 0.8 | 7.7 |
| Early ten days of the month | | | 5.9 | 16.5 | −2.7 | 57.8 |

EXAMPLE 3

Hardening Test

Figure 12:
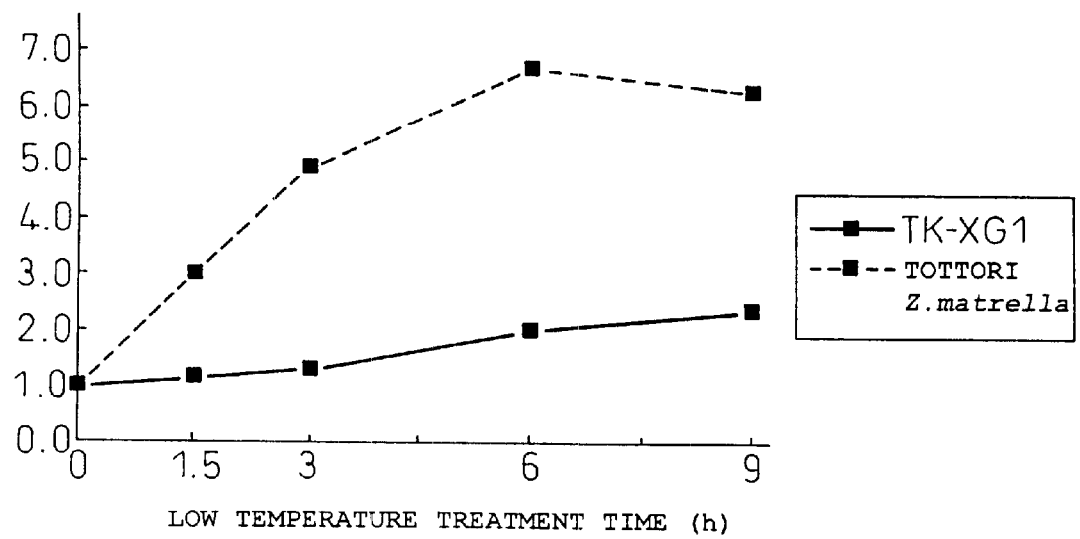
FIG. 12 is an electrical conductivity (EC) point line graph for TK-XG1 and Tottori Z. matrella treated at a low temperature of −15° C. for 0, 1.5, 3, 6 and 9 hours. The data are expressed in terms of the rate of change in EC due to low temperature treatment (an increase in EC occurs upon cellular destruction by freezing), where 1 is defined as the EC before treatment at the low temperature of −15° C.

After one month of raising TK-XG1 and Tottori Z. matrella established in a wagnel pot in an artificial weather apparatus (LH-200RDZ, Nippon Medical & Chemical Instruments Co, Ltd.) at 4±2° C. under 50,000 lux, a low temperature resistance test was conducted in a freezer (MDF-293AT, SANYO). Approximately 50 mg of live leaves were collected, weighed and wrapped in aluminum foil, and after freezing in freezers set to −15° C. and −10° C. for periods of 0, 1.5, 3, 6 and 9 hours, each sample was taken out, immersed in 20 ml of distilled water and allowed to stand for 24 hours in a refrigerator (5° C.), and an electric conductivity meter (Model SC82 Personal SC Meter, YOKOGAWA) was used to measure the elactric conductivity (EC); the EC values for the Tottori Z. matrella and TK-XG1 prior to the start of low temperature treatment were each defined as 1.0, and the changes in time were observed to evaluate the degree of freezind-induced cell disruption. Almost no cell disruption occurred in either the TK-XG1 or Tottori Z. matrella when treated at −10° C., but when treated at −15° C. both exhibited an increase in EC due to cell disruption (FIG. 12). However, TK-XG1 showed a gentler slope for the EC up to 3 hours of low temperature treatment compared to the Tottori Z. matrella, suggesting that it was more resistant to freezing-induced cell disruption.

EXAMPLE 4

Growth Test with TK-XG1

Figure 13A:
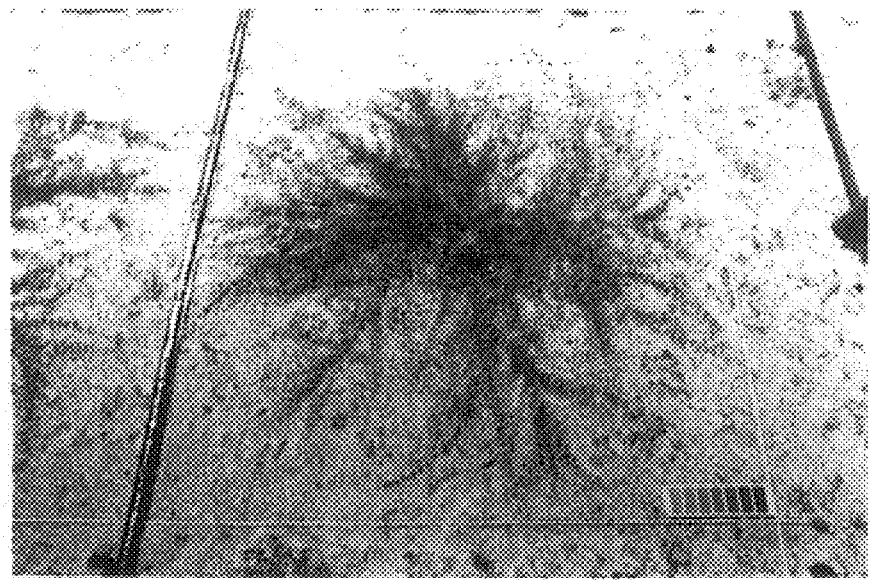
FIG. 13a is TK-XG1 and FIG. 13b is Tottori Z. matrella.
Figure 13B:
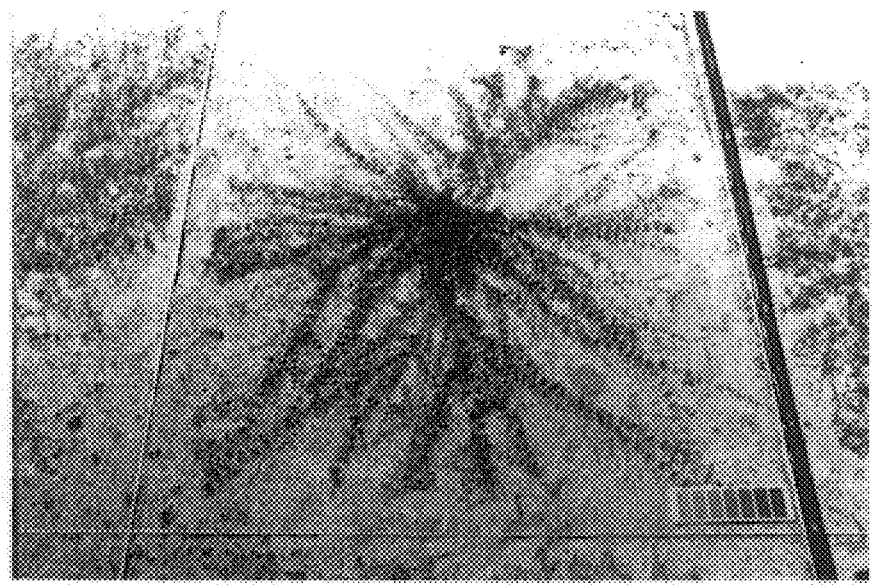
Figure 14A:
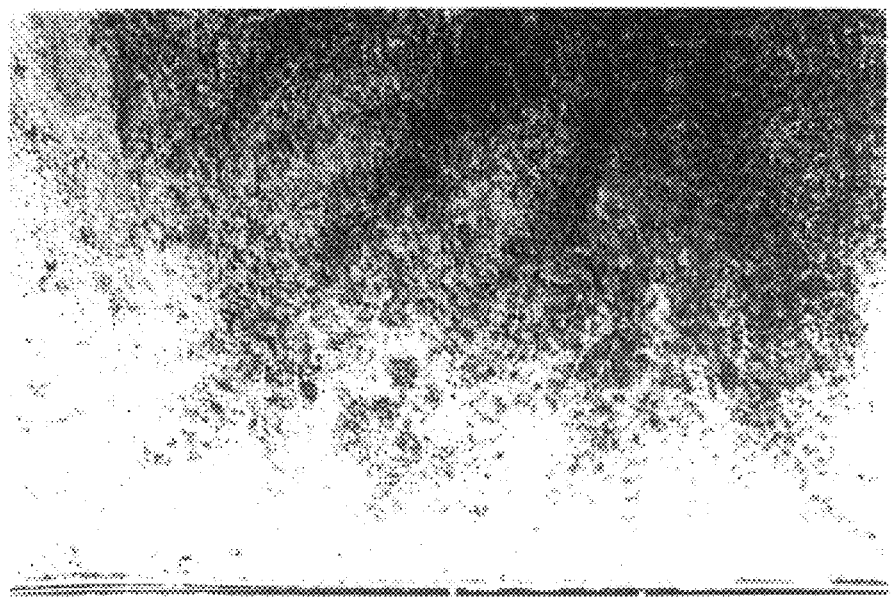
FIG. 14a is of FIG. 13a and FIG. 14b is of FIG. 13b.
Figure 15A:
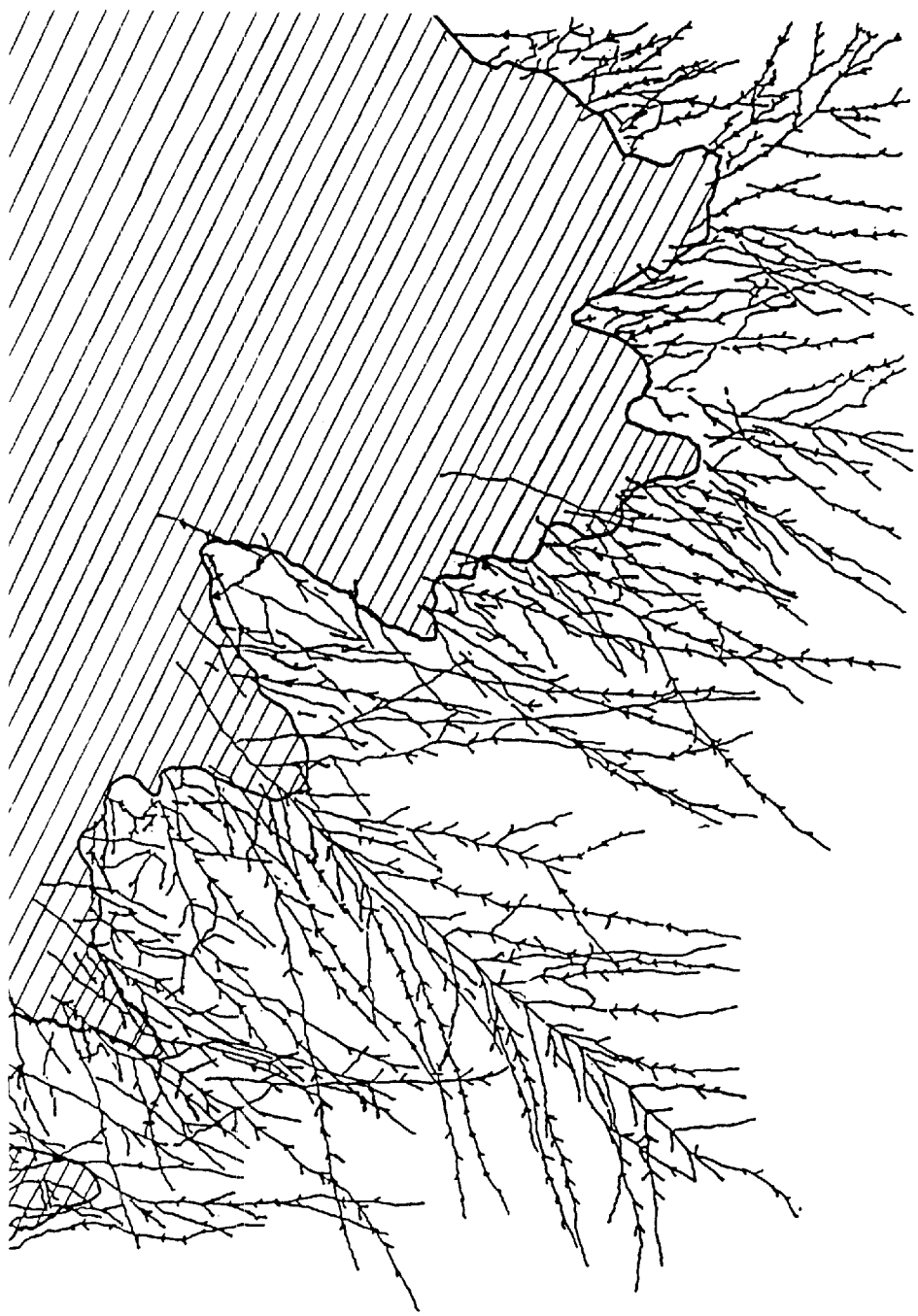
FIG. 15 is a line diagram showing extension of stolons, where FIG. 15a was drawn from FIG. 14a and FIG. 15b was drawn from FIG. 14b. In each drawing, the shaded region is the total-covering dense region. The high lateral stolon growth in the case of TK-XG1 rapidly formed a dense region with extension of stolons.
Figure 16:
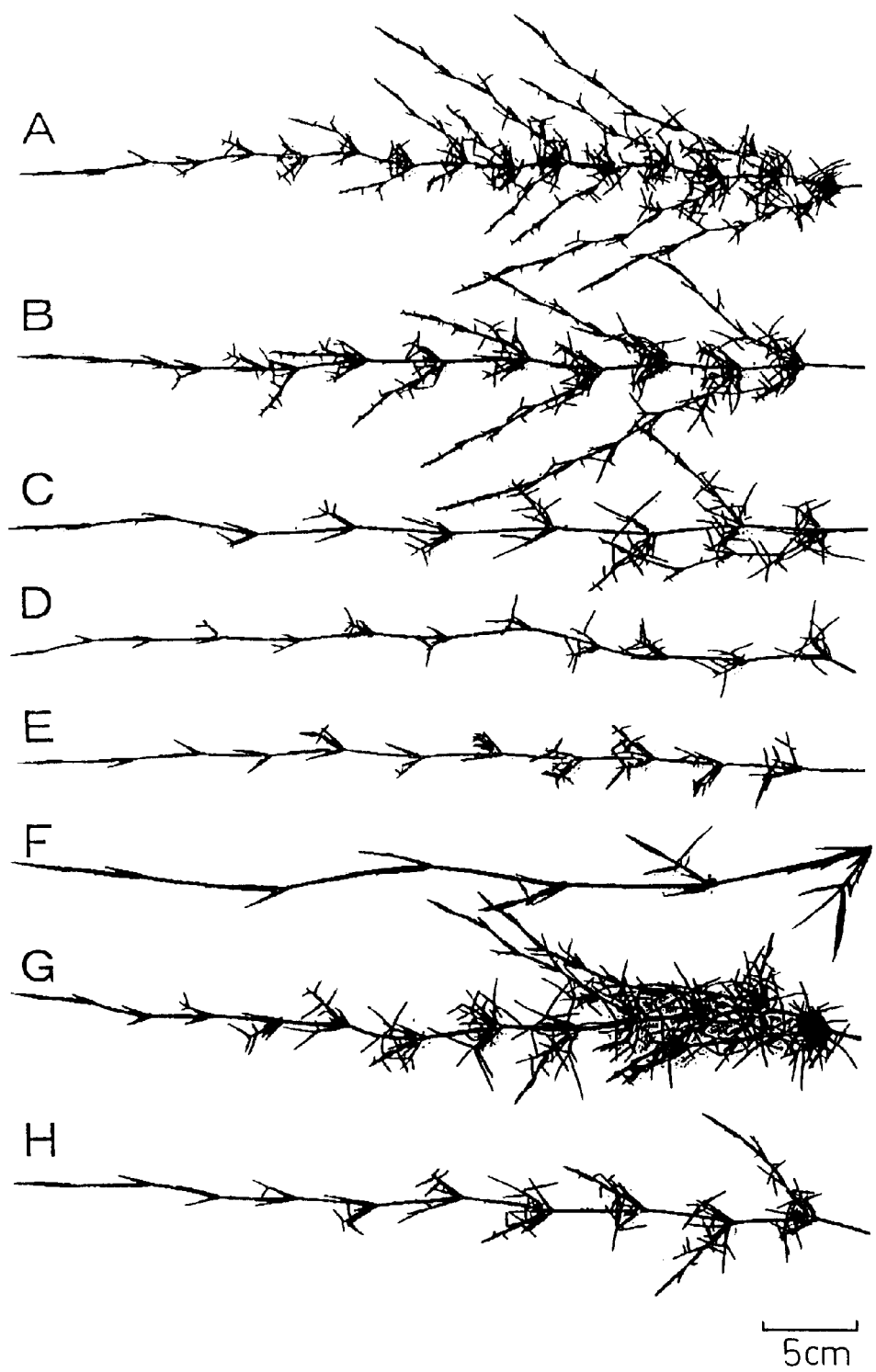
FIG. 16 is a comparative line diagram of stolons, cut off 43.0 cm-long from their tips of stolons for 8 representative lines.
Figure 17:
FIG. 17 is a photograph showing stolen extensions of TK-XG1 and Tottori Z. matrella (see Table 10).

Soil comprising a mixture of masatsuchi and sand in a ratio of 7:3 with a mixture of 100 kg/m$^3$ of hard foaming sintered diatomite granules, 1.5 kg/m$^3$ of citrate soluble slow acting fertilizer and 10 kg/m$^3$ of a special fermented fertilizer (research field, Kaisui Chemical Industry Co., Ltd. at 535 Hamakata, Hofu City, Yamaguchi Prefecture) was used, and 5-node stolons were transplanted at the center of a 2.0 m square section on Sep. 17, 1997 and supplied with 12.5 g/m$^2$ of a chemical fertilizer containing nitrogen:phosphoric acid:potassium at 10:10:10 wt % (Starmine: Nitto FC Co., Ltd.) at a frequency of once a month to promote growth. The full photographs on Oct. 19, 1998 are shown in FIG. 13a (TK-XG1) and FIG. 13b (Tottori Z. matrella). Representative partially enlarged photographs are shown in FIG. 14a (TK-XG1) and FIG. 15b (Tottori Z. matrella), and line diagrams showing the extension of stolons therefrom are shown in FIG. 15a (TK-XG1) and FIG. 15b (Tottori Z. matrella). Also, FIG. 16 shows a comparative line diagram of 43.0 cm-long representative stolon tips for 8 lines grown in the same manner.

Turfgrass internode length and stolon length are determined by the growing conditions. For example, the internode length of stolons that freely extend from the soil surface tends to be shortened, and the growth of lateral stolons is often suppressed. Growth is also suppressed when the stolons overlap or are inhibited by some physical obstacle. Spindly growth usually results from shading from sunlight. For an accurate comparison, therefore, it is necessary to collect and compare stolons extending under the same growth conditions, attached to the soil surface and free from obstacles. The front part of the stolons were taken to a length equal to 20 nodes (43.0 cm) of TK-XG1 including the shoot apex. Tables 10 and 11 show the internode distances and stolon extension as actually measured based on FIG. 16. In this example, as shown in FIG. 16, the still extending immature internodes were within about 10 cm, and this range was excluded from the measurement.

Figure 14B:
FIG. 14 is a partial enlarged photograph of FIG. 13, where

TK-XG1 was compared with its parental strain (starting material for mutagenic manipulation), the Tottori *Z. matrella*, and found to have roughly the same extension overall (see FIGS. 13*a*, 13*b*), but its shorter internode distance and clearly greater lateral stolon growth resulted in a notably larger area of coverage (dense planting section) (see FIGS. 14-*a*, -*b* and FIGS. 15*a*, 15*b*). A shorter internode distance and greater lateral stolon growth increases the covering speed to form a denser ground cover, while the strong creeping property of TK-XG1 (property of attaching to soil and extending) increases the overlap of stolons in the ground and enhances the soil surface protection; the recovery after injury to the grass layer surface by spike injury and the like is also more rapid, a turf layer with excellent elasticity can be formed, and thus in practical terms it is possible to provide turfgrass of much higher value than conventional Manilagrass (*Zoysia matrella*) or other Eragrostoideae turfgrass.

For data processing, one maximum and minimum value of the measured internode lengths for each variety were discarded and only the remaining values were used, in order to eliminate the abnormal values. Considering the different sensitivities of the different plant varieties depending on the environmental conditions, soil form and fertilization method, the ratio of internode length of TK-XG1 was in the range of 0.938–0.651 with respect to 1.0 for Tottori *Z. matrella* and Meyer, and was significantly dwarfed. Both Tottori *Z. matrella* and Meyer were used as comparative controls because they are representative turfgrass varieties of the subfamily Eragrostoideae and the internode measurement data was plenteous for this example, so that they could serve as accurate standards for data processing. Incidentally, since Eragrostoideae turfgrass generally undergoes varying internode growth depending on the growing conditions, it is preferred for comparative evaluation to be carried out according to this example; however, it is at least necessary to compare the stolons under conditions in which they are attached to the soil surface and extend without obstacles. It is also necessary to select stolons with continued growth without injury to the shoot apex. The internode near the tip of the main stolon lengthens with growth and extension of the main stolon, and internode extension ceases with maturity. It is therefore necessary to make the comparison of the area near the tip end excluding the immature tip. For this example, as shown in FIG. 16, the still extending immature internodes were about 10 cm, and these sections were excluded from measurement of the internode lengths. In practice it is preferred for the lateral stolons to follow up near to the tip end of the main stolon to create a dense vegetative region. As shown in Table 4, the blade width was narrower and the blade length was slightly shorter compared to its parental strain Tottori *Z. matrella*.

The ratio of the main stolon growth to the total lateral stolon growth was in the range of 1.2–1.4 times that of the Tottori *Z. matrella* and 1.4–1.8 times that of the Meyer.

TABLE 10

Internode length of vegetative stolons attached to soil surface, excluding part of a stolon, cut off 10 cm long from its tip

| | Internode length (mm) from section excluding 100 mm tip (330 mm) | | | | | | | | | | |
|---|---|---|---|---|---|---|---|---|---|---|---|
| | 1 | 2 | 3 | 4 | 5 | 6 | 7 | 8 | 9 | 10 | 11 |
| TK-XG1 | 26.4 | 25.9 | 28.4 | 25.5 | <u>24.8</u> | (24.6) | 26.3 | 24.9 | 27.3 | (29.8) | <u>28.8</u> |
| Tottori *Z. matrella* (1) | (17.5) | 32.6 | <u>38.1</u> | (42.5) | 36.6 | 34.9 | 36.9 | <u>30.7</u> | — | — | — |
| Wintercarpet (2) | 48.7 | 49.1 | 51.7 | (52.2) | 44.2 | (40.6) | — | — | — | — | — |
| Winterfield (3) | 41.1 | 35.7 | 38.0 | 39.6 | 36.3 | (34.4) | 40.5 | (41.1) | — | — | — |
| Victoria (4) | 36.5 | (40.1) | 40.1 | 40.1 | 37.2 | (35.0) | 39.9 | — | — | — | — |
| Miyako (5) | 74.6 | (69.3) | 76.5 | (79.9) | — | — | — | — | — | — | — |
| Meyer (6) | 34.7 | 32.5 | (39.5) | <u>38.9</u> | 38.9 | 34.8 | 35.1 | (27.3) | <u>32.3</u> | — | — |
| Emerald (7) | (40.9) | 41.9 | 43.4 | 44.2 | (46.5) | 45.1 | 41.9 | — | — | — | — |

| | Average of values excluding abnormal values Av. [R] | Ratio of maximum for TK-XG1 and minimum of each control variety | Ratio of minimum for TK-XG1 and maximum of each control variety |
|---|---|---|---|
| TK-XG1 | 26.5 [4.0] | | |
| Tottori *Z. matrella* (1) | 35.0 [7.4] | 0.938 | 0.651 |
| Wintercarpet (2) | 48.4 [7.5] | — | — |

TABLE 10-continued

Internode length of vegetative stolons attached to soil surface, excluding part of a stolon, cut off 10 cm long from its tip

|  |  |  |  |
|---|---|---|---|
| Winterfield (3) | 38.5 [5.4] | — | — |
| Victoria (4) | 38.8 [3.6] | — | — |
| Miyako (5) | 75.6 [1.9] | — | — |
| Meyer (6) | 35.3 [6.6] | 0.892 | 0.638 |
| Emerald (7) | 43.3 [3.2] | — | — |

(1) A Manilagrass (*Zoysia matrella*) variety produced by the Tottori Sod Producers Association: starting material for TK-XG1
(2) Acinic Manilagrass developed by Sumitomo Metal Industries, KK.
(3) Same as above
(4) Improved variety bred by Dr. V. Giveault et al., obtained by crossbreeding Japanese turfgrass with El Toro (an improved variety of *Zoysia japonica*) as the parent.
(5) Hybrid variety of *Zoysia japonica* × Manilagrass, bred by Japan Turf, KK.
(6) Line selected from *Zoysia japonica* seeds, bred by cooperation between the U.S. Dept. of Agriculture test grounds and the Golf League Green Section
(7) Line selected from hybrid variety of *Zoysia japonica* and *Zoysia tenuifolia*, jointly bred by the U.S. Dept. of Agriculture and the All-American Golf Association
(8) The maximum and minimum value ratios were also calculated after excluding the maximum and minimum values (in brackets) for the internode lengths for each variety, in order to avoid inordinately large ranges due to abnormal values.
(9) The underlined measured values are the maximum and minimum values of the internode lengths after exclusion of the abnormal values (in brackets).

TABLE 11

Ratios of lengths of main stolons which are cut off 43 cm from their tips to lengths of total lateral stolons of growing stolons attached to the soil surface

|  |  | Total lateral stolon length[1] (cm) | Total lateral stolon length/main stolon length 43 cm | Lateral stolon/main stolon ratio for TK-XG1 with respect to 1.0 for control variety[2] |
|---|---|---|---|---|
| TK-XG1 | ① | 111.6 | 2.60 | — |
|  | ② | 118.4 | 2.75 | — |
|  | ③ | 101.9 | 2.37 | — |
| Tottori | ① | 84.1 | 1.96 | 1.33 |
| *Z. matrella* | ② | 89.1 | 2.07 | 1.33 |
|  | ③ | 81.3 | 1.89 | 1.25 |
| Wintercarpet | ① | 35.4 | 0.82 | — |
|  | ② | 34.2 | 0.80 | — |
|  | ③ | 36.7 | 0.85 | — |
| Winterfield | ① | 12.0 | 0.28 | — |
|  | ② | 12.5 | 0.29 | — |
|  | ③ | 11.3 | 0.26 | — |
| Victoria | ① | 15.1 | 0.35 | — |
|  | ② | 15.7 | 0.37 | — |
|  | ③ | 14.2 | 0.33 | — |
| Miyako | ① | 8.3 | 0.19 | — |
|  | ② | 8.5 | 0.20 | — |
|  | ③ | 8.1 | 0.19 | — |
| Meyer | ① | 63.5 | 1.48 | 1.76 |
|  | ② | 65.7 | 1.53 | 1.80 |
|  | ③ | 71.4 | 1.66 | 1.43 |
| Emerald | ① | 33.6 | 0.78 | — |
|  | ② | 34.1 | 0.79 | — |
|  | ③ | 39.8 | 0.93 | — |

[1]①, ② and ③ are the series numbers for each experiment group.
[2]Calculated for each experiment group in the following manner: for example, for experiment group ①, 2.60/1.96 = 1.33.

EXAMPLE 5

Production of Hybrid Variety Inheriting the Character of TK-XG1 of the Invention In order to confirm that the new character of the TK-XG1 of the invention can be inherited and transferred by crossbreeding with Eragrostoideae plant, it was crossbred with Miyako (hybrid variety of *Zoysia japonica*, by Japan Turf, KK.) in an attempt to produce a derivative variety.

As a result, the Miyako that was crossbred with the TK-XG1 exhibited a dark purplish red color in the stolons due to anthocyanins under the same conditions, whereas the newly produced variety had yellow-green stolons with substantially no accumulation of anthocyanins, as one of the unique characteristics of TK-XG1. The production process and some properties of the new artificially crossbred variety produced thereby will be described below.

Crossbreeding was carried out with Miyako as the female and TK-XG1 as the male. The crossbreeding method was according to "Agricultural Experimental Manual of Plant Production" (Hinata, Y. and Hashibia, T. ed., 1995, Softscience Publications, pp.263–268).

After crossbreeding, the product was raised and matured in a greenhouse and seeds were collected after 40 days. After indoor storage for 3 months to improve the germinating rate of the collected seeds, the fertile seeds and non-fertile seeds were separated by the alcohol selection method. A total of 98 settling seeds were selected for use and the germinating rate was increased by treatment with 0.5% NaOH (see Hirayoshi, I., Matsumura, M., Iwata, E., "Dissemination and Growth of Useful Wild Grasses", Gifu University, Agricultural Dept. Laboratory Report, No.28, 1969, pp.239–251).

The 98 seeds treated with 0.5% NaOH were placed on water-absorbed filter paper stretched over a Petri dish, and a germination experiment was commenced under conditions of 35° C., 8,500 lux in an artificial weather apparatus.

A total of 23 seeds germinated among the 98 seeds, and on the fifth day after germination the young buds were transferred to plastic pots containing autoclave-sterilized rice cultivating soil (Kumiai Ube Special Soil #2 by Ube Industries, Ltd., containing 0.2 g each of nitrogen and phosphoric acid and 0.33 g of potassium per kg).

The eighteen seedlings that were raised from the 23 germinated seeds were transferred to growing pots. The cultivating soil composition of the transfer pot soil was a mixture of sea sand:hard forming sintered diatomite granules:peat moss:woody compost (bark) at 6:2:1:1, also containing 2% citric acid soluble slow acting fertilizer at a concentration of 1.5 kg/m$^3$, and the plants were raised with water sprinkling in a greenhouse at 28° C.±3° C. The 18 young plants were set in the same section and 125 fruiting seeds were collected, stored, selected and germinated by the same method to obtain 19 young plants. Of these, one variety was obtained having stolons exhibiting no purplish red color and containing no anthocyanins. The blade width, internode length and stolon thickness of the resulting young plant of this variety were measured on Nov. 22, 1999. Table 14 shows the data for the variety that exhibited no purplish red color in the stolons.

It is known that crossbred varieties can be produced, even in the case of distant relative crossbreeding, so long as the plants have a matching base number of chromosomes (See, for example, "Turfgrass and Its Varieties", pp.126–130 cited above.), and this example demonstrates the possibility of developing crossbred varieties that inherit the invented genetic character of TK-XG1.

TABLE 14

♀Miyako × ♂TK-XG1: Growth conditions of variety F$_2$
(observed Nov. 22, 1999)

|  | ♀Miyako | ♂TK-XG1 | F$_2$ Variety exhibiting no purplish red color |
|---|---|---|---|
| Purplish red color in stolons | present | absent | absent |
| Blade width (mm) | 3.6 | 2.0 | 2.5 |

It is not clear whether the various characteristics of the new variety of the invention each appeared independently or whether a mutation in a single gene expresses these various phenotypes, but in general consideration of mutation methods it may be more naturally assumed that the completely new multiple Manilagrass characteristics exhibited by the variety of the invention are independent characteristics due to mutations at multiple loci. Each new characteristic is absent from the parental strain and each is independently novel, practical and useful. By using these individual genotypes in variety-producing methods such as crossbreeding, it is possible to produce derivative varieties with new practical uses, utilizing the four aforementioned genotypes of the invention.

Comments for Cultivation

The TK-XG1 of the invention can be cultivated at production field by the same methods as Tottori Z. matrella. However, because of its higher growth rate compared to Tottori Z. matrella, it is preferably given a slight excess of fertilizer while observing the condition of growth. Growth by multiple shoots is also possible. For practical use, it can be easily cultivated at the same production field by the same methods as Tottori Z. matrella. Cultivation management can also reinforce certain characteristics required by the purpose for which the TK-XG1 of the invention is to be used.

I claim:

1. The TK-XG1 variety of Manilagrass deposited as FERM BP-7837 characterized by retaining its green leaves under a condition where the mean temperature of a period of ten days is 6° C. or below and the lowest temperature in this period is −1° C. or below, but not less than −15° C., and by containing substantially no anthocyanins throughout the year, and by that the length of internode of the main stolon except the immature internode of the front part of the main stolon, which extends when attached to the soil surface under obstacle-free growth conditions, is about 0.9—about 0.6, where 1.0 is defined as the length for conventional Tottori Z. matrella, and also by that the ratio of the main stolon length to the total lateral stolon length, measuring the total length of lateral stolons developing from the main stolon based on a main stolon length corresponding to at least 20 nodes from the tip of the main stolon of the turfgrass of the invention, in stolons extending under obstacle-free growth conditions when attached to the soil surface, is at least 1.2 times compared to conventional Tottori Z. matrella.

* * * * *